(12) United States Patent
Nakamoto et al.

(10) Patent No.: US 6,183,711 B1
(45) Date of Patent: Feb. 6, 2001

(54) APATITE-FORMING-SYSTEMS: METHODS AND PRODUCTS

(76) Inventors: Tetsuo Nakamoto, 4228 Beaune Dr., Kenner, LA (US) 70065; William B. Simmons, Jr., 4976 Saint Roch Ave.; Alexander U. Falster, 4617 Eastern St., both of New Orleans, LA (US) 70122

( * ) Notice: Under 35 U.S.C. 154(b), the term of this patent shall be extended for 0 days.

(21) Appl. No.: 08/579,121

(22) Filed: Dec. 27, 1995

(51) Int. Cl.$^7$ .................................................. C01B 25/26
(52) U.S. Cl. ...................... 423/308; 423/309; 423/311; 544/273
(58) Field of Search ........................... 544/273; 514/263, 514/264; 424/602; 423/308, 309, 311

(56) References Cited

U.S. PATENT DOCUMENTS 5,436,258    7/1995    Blake et al. ......................... 514/372

OTHER PUBLICATIONS

Hashimoto, et al. Effects of maternal caffeine intake during lactation on molar enamel surfaces in new–born rats. Archs oral Biol. vol. 37, pp. 105–109, 1992.

Falster et al. Physical Examination of Caffeine's effects on the enamel surface of first molar in new–born rats. Archs oral Biol. 37, pp. 111–118, 1992.

Nakamoto et al. Cariogenic effect of caffeine intake during lactation on first molars of newborn rats. Archs. oral Biol. 38, 919–922, 1993.

Falster et al. The effect of prenatal caffeine exposure on the enamel surface of the first molars of newborn rats. Archs oral Biol. 38, 441–447, 1993.

Nakamoto et al. Protein–energy malnutrition in rats during pregnancy modifies the effects of caffeine on fetal bones. J. Nutr. 116, 663–640, 1986.

*Primary Examiner*—Richard L. Raymond
(74) *Attorney, Agent, or Firm*—Michael L. Murray

(57) ABSTRACT

Methods comprise contacting apatite-forming-systems with partially alkylated xanthines. The methods include pharmaceutical applications of partially alkylated xanthines to mitigate the effects of hard tissue diseases. Products comprise apatite formed from apatite-forming-systems contacted with partially alkylated xanthines.

8 Claims, 20 Drawing Sheets

FIG. 1 *IN VIVO* EXPERIMENTAL PLAN

APATITE-FORMING-SYSTEMS: METHODS AND PRODUCTS

BACKGROUND OF THE INVENTION

Field of the Invention

The present invention relates to making and using apatite crystals, both in vitro and in vivo, and to the mitigation of the effects of hard tissue diseases.

Natural Sources of Apatite

Calcium hydroxyapatites, a complex calcium phosphate ($Ca_5(PO_4)_3OH$) in crystalline form, occur naturally as geological deposits and in normal biological tissues, principally bone, cartilage, enamel, dentin, and cementum of vertebrates and in many sites of pathological calcifications such as blood vessels and skin. Essentially none of the geological and biological apatites are "pure" hydroxyapatite since they contain a variety of other ions and cations and may have different ratios of calcium to phosphorous than the pure synthetic apatites. In general, the crystals of pure synthetic apatites, geological apatites and many impure synthetically produced apatites are larger and more crystalline than the biological crystals of bone, dentin, cementum and cartilage.

The terms "crystal" and "crystallite" may be used interchangeably in most respects; "crystallite" simply means a small crystal. A crystal is a homogeneous, solid body of a chemical element, compound, or isomorphous mixture, having a regular repeating atomic arrangement of atoms that may or may not be outwardly expressed by planar faces.

The calcium-phosphate crystals of the bones of essentially all vertebrates have the basic crystal structure of hydroxyapatite as determined by X-ray diffraction. Indeed, the calcium-phosphate crystals of essentially all of the normally mineralized tissues of vertebrates, including enamel, dentin, cementum, and calcified cartilage, have the same general crystal structure. For the purposes of the present invention, these tissues are called "hard tissues".

However, the crystals of calcium phosphate found in hard tissues such as bone also contain other atoms and ions such as acid phosphate groups ($H_2PO_4$), and carbonate ions, which do not occur in pure, synthetic hydroxyapatite. There is also good evidence that bone crystals either do not contain hydroxyl groups, or contain only very few such groups (Rey et al. (1995) Hydroxyl groups in bone mineral, Bone 16: 583–586) and is therefore more appropriately referred to as "apatite" rather than "hydroxyapatite." Moreover, many of the carbonate and phosphate groups in bone crystals are, from the structural and physical chemical points of view, unstable and very reactive, thus providing certain physical chemical and biological functional and chemical features important in the formation and dissolution of the crystals in biological tissues.

Recent $^{31}P$-nuclear magnetic resonance spectroscopy studies have demonstrated that the short-range order or environment of the $H_2PO_4$ groups in bone crystals are distinctly different than the $H_2PO_4$ groups in synthetic apatites and other related calcium-phosphate crystals (Wu, Ph.D. thesis M.I.T., "Solid state NMR study of bone mineral," Aug. 1992). These differences in chemical, structural, and short range order of the bone crystals compared with pure, synthetic hydroxyapatite also reflect significant differences in their reactivity and hence in their potential function in a biological environment.

The crystals of bone, dentin and cementum are very small, irregularly shaped, very thin plates whose rough average dimensions are approximately 10 to 50 angstroms in thickness, 30 to 150 angstroms in width, and 200 to 600 angstroms in length. This results in their having a very large surface area to present to the extracellular fluids which is critically important for the rapid exchange of ions with the extracellular fluids. This "ion-reservoir" function of the inorganic crystals is very important for a number of critical biological functions.

For a description of the determination of the size of bone crystals, see Ziv, V., and Weiner, S. (1994) Bone Crystal Sizes: A comparison of transmission electron microscopic and X-ray diffraction line width broadening techniques. Connective Tissue Research, 30: 165–175; also Azaroff, L. V. (1968) Elements of X-Ray Crystallography, McGraw-Hill; also Hurlbut, C. S., & Klein, C. (1977) Manual of Minerology, 19th ed., John Wiley & Sons. Most investigators of bone structure prefer to rely on measurements of X-ray diffraction reflection line widths. This parameter is directly related to coherence length, that is the average distance between lattice dislocations in a given direction.

Synthetic Sources of Apatite

Synthetic apatites are highly diverse. For example, the characterization of four commercial apatites was reported by Pinholt, et al., J. Oral Maxillofac. Surg. 50(8), 859–867 (Aug. 1992); J. Cariofac. Surg. 1(3), 154–160 (Jul. 1990) reports on a protein, biodegradable material; Pinholt, et al., Scand. J. Dent. Res. 99(2), 154–161 (Apr. 1991) reports on the use of a bovine bone material called BiO-OSS.™.; Friedman, et al., Arch. Otolaryngol. Head Neck Surg. 117 (4), 386–389 (Apr. 1991) and Costantino, et al., Arch. Otolaryngol. Head Neck Surg. 117(4), 379–384 (Apr. 1991) report on a hydroxyapatite cement; Roesgen, Unfallchirurgie 258–265 (Oct. 1990), reports on the use of calcium phosphate ceramics in combination with atogeneic bone; Ono, et al., Biomaterials 11(4), 265–271 (May 1990) reports on the use of apatite-wollastonite containing glass ceramic granules, hydroxyapatite granules, and alumina granules; Passuti, et al., Clin. Orthop. 248, 169–176 (Nov. 1989) reports on macroporous calcium phosphate ceramic performance; Harada, Shikwa-Gakuho 89(2), 263–297 (1989) reports on the use of a mixture of hydroxyapatite particles and tricalcium phosphate powder for bone implantation; Ohgushi, et al., Acta Orthop. Scand. 60(3), 334–339 (1989) reports on the use of porous calcium phosphate ceramics alone and in combination with bone marrow cells; Pochon, et al., Z-Kinderchir. 41(3), 171–173 (1986) reports on the use of beta-tricalcium phosphate for implantation; and Glowacki, et al., Clin. Plast. Surg. 12(2), 233–241 (1985), reports on the use of demineralized bone implants.

Apatite-Forming-Systems

Synthetic calcium hydroxyapatite is formed in the laboratory either as pure $Ca_5(PO_4)_3$ (OH) or hydroxyapatite that is impure, containing other ions such as carbonate, fluoride, chloride for example, or crystals deficient in calcium or crystals in which calcium is partly or completely replaced by other ions such as barium, strontium and lead. Systems for forming apatite by precipitating solutes are known from the literature. In these processes, hydroxyapatite precipitates in very finely crystalline form in nearly all solutions.

Some examples of methods for the precipitation of hydroxyapatite, the properties of the apatite product, and possible applications are discussed below. For the purposes of this invention, the term "apatite" signifies any of the forms of apatite in which the hydroxyl groups are replaced by other anions.

It is known from U.S. Pat. No. 4,274,879, for example, to prepare hydroxyapatite by mixing milk of lime with at least 60% phosphoric acid in stoichiometric amounts at temperatures of 80° C.–85° C., and a pH of the reaction solution of about 9.0–11.0 in a continuous reaction. The products obtained are suitable for preparing bone replacement parts by sintering at temperatures of 700° C. They are unsuitable as tooth-cleaning substances on account of their fineness. Additional examples of such methods, products, and applications are disclosed in U.S. Pat. Nos. 4,324,772 and 4,849,193.

Apatites in which the $OH^-$ is replaced with simple anions, including $F^-$, $Br^-$, $I^-$, or carbonate, may be prepared by modifying the process for preparing hydroxyapatite. Apatite derivatives in which calcium is replaced by metal ions, such as paramagnetic, radiopaque, or radioactive metal ions, may also be prepared and used within the scope of the present invention. Useful apatites may also be prepared by replacing phosphate with oxyanions or tetrahedral anions containing radiopaque or radioactive metal species. Stoichiometric pure hydroxyapatite has a Ca:P ratio of 1.67:1. The major impurity found in hydroxyapatite is tricalcium phosphate, $Ca_3(PO_4)_2$, known as "TCP." This impurity can be detected by deviation from the 1.67:1 Ca:P ratio (for large amounts of impurity) or by X-ray diffraction for impurity levels down to 1 percent. Stoichiometric hydroxyapatite is prepared by adding an ammonium phosphate solution to a solution of calcium/ ammonium hydroxide. To minimize the amount of TCP formed, it is important to have excess calcium throughout the addition process.

U.S. Pat. No 5,460,803 to Ming S. Tung issued Oct. 24, 1995 discloses two apatite-forming-systems. The first system particularly involves the use of amorphous calcium compounds such as: amorphous calcium phosphate, amorphous calcium phosphate fluoride, amorphous calcium carbonate phosphate, and amorphous calcium carbonate phosphate fluoride. The compounds have the highest solubilities, fastest formation rates and fastest conversion rates to apatite among all the calcium phosphates under physiological conditions. Moreover, in the presence of fluoride the amorphous compounds convert rapidly to fluoride containing apatite. In a unique aspect, the method takes advantage of the solvent qualities of ethanol.

In a second apatite-forming-system disclosed by U.S. Pat. 5,460,803, the amorphous calcium compounds are formed, in situ, as an intermediate prior to the precipitation of the apatite. The method uses carbonated solutions containing calcium ions, fluoride ions, carbonate ions and phosphate ions, maintained under a pressurized carbon dioxide atmosphere. Under the pressurized carbon dioxide atmosphere, the solutions have a lower pH and are stable. When applied under atmospheric pressure, carbon dioxide escapes, causing the pH to increase. This increase in pH results in a supersaturated solution and ultimately rapid precipitation of apatite.

Effect of Electrical Charge and Stress on In Vivo Apatite-Forming-Systems

Hydroxyapatite is piezoelectric; that is, it generates an electric charge when mechanically stressed. The electric signals generated by hydroxyapatite when bone is placed under stress ("bone talk") are detected by nearby bone cells, stimulating them to increase the production of hydroxyapatite. This increase in production of hydroxyapatite due to "bone talk" appears to be part of a feedback mechanism causing bone to be strengthened automatically at points of stress concentration. This feedback mechanism is weakened or interrupted in areas surrounding a bone fracture since stress concentrations at the fracture are typically nil. A similar feedback mechanism seems to control the mineral content of intact bone. When normal "bone talk" is no longer communicated to surrounding cells, the production of hydroxyapatite decreases and osteoporosis (meaning "brittle bones") can result. Restoration of the piezoelectric signal can slow or reverse this condition.

Optimum waveforms, generated by alternating current signals, can nearly double the rate of bone healing in ordinary fractures, and restart healing in nonunion fractures, i.e. those fractures in which normal healing has stopped without rejoining the pieces of the broken bone. The conventional treatment of non-union fractures involves surgical procedures which are often unsuccessful and invariably increases both the discomfort and expense incurred by the patient. The use of electronic stimulation as a method of treating fractured bones has reduced the reliance on conventional surgery. See Donahue, R.C.T., et al, Optimization of electric field parameters for the control of bone remodeling: exploitation of an indigenous mechanism for the prevention of osteopenia. J Bone Miner Res 1993; 8 Suppl 2: S573–81; Chilibeck P D. Sale D G. Webber C E. Exercise and bone mineral density (1995) Sports Med; 19(2): 103–22.

Disorders of Hard Tissue

Except for the common cold, dental caries (tooth decay) is the most prevalent human disorder. See, The Merck Manual, Sixteenth Edition, p. 2480. Many steps have been taken to reduce dental caries and tooth decay, such as fluoridation and improved dental care, nevertheless tooth decay continues to be a significant problem. See, Featherstone, An Updated Understanding of the Mechanism of Dental Decay and its Prevention, Nutrition Quarterly, Vol. 14, No. 1, 1990, pp. 5–11.

To protect a normal tooth, a thin layer of dental enamel forms a protective coating over the tooth. This coating consists mainly of calcium, phosphate, and other ions in a hydroxyapatite-like structure. The enamel contains 2–5 percent carbonate; this carbonate content makes the enamel susceptible to acid dissolution. See, Featherstone, id. at 6.

Teeth vary considerably in their susceptibility to dissolution, and large crystallite size is correlated with resistance to dissolution (Besic et al, JADA, 91:594–601 (1975).

Bone Formation and Renewal

Bone is a highly specialized connective tissue with unique mechanical properties derived from its extensive matrix structure. A network of fibrous bundles composed of collagen is presumed to provide the tension-resistant behavior of bone. In addition, other materials including proteoglycans, noncollagenous proteins, lipids and acidic proteins associated with a mineral phase consisting primarily of poorly crystallized hydroxyapatite are deposited in the extensive matrix architecture of bone. Bone tissue is continuously renewed, by a process referred to as remodeling, throughout the life of mammals. This physiologic process might serve to maintain the properties of a young tissue.

The processes of bone formation and renewal are described by Mundy in "Bone Remodeling and Its Disorders" (1995, pub. Martin Dunitz). Osteogenesis vis-a-vis morphogenesis and growth of bone is presumably carried out by "osteoblasts" (bone-forming cells). Remodeling of bone is apparently brought about by an interplay between the activities of the bone-resorbing cells called "osteoclasts" and the bone-forming osteoblasts. The bony skeleton is thus not only an architectural structure with a mechanical function but also is a living tissue capable of growth, modeling, remodeling and repair. Since these processes are carried out by specialized living cells, chemical (pharmaceutical/hormonal), physical and physicochemical alterations can affect the quality, quantity and shaping of bone tissue.

The adult skeleton is composed of 80% cortical and 20% trabecular bone. Bone matrix is composed of 25% collagen, 65% inorganic material, and 10% non-cellular proteins (i.e., osteocalcin, silaoprotein, proteoglycans and osteonectin) and lipids. The term "mature bone" relates to bone that is mineralized, in contrast to non-mineralized bone such as osteoid. Osteoblasts synthesize and secrete Type 1 collagen and mucopolysaccharides to form the bone matrix which is laid down between the thin layers of osteoid. The layers are subsequently mineralized with 99% of the body's calcium found in the bone as a calcium phosphate complex with hydroxyapatite.

Conditions that Affect Bone Strength

A number of dangerous and painful disabilities are caused by the excessive resorption of bone. For example, rheumatoid arthritis and periodontitis (both associated with erosive joint disease) osteoporosis, and the failure of prostheses to remain tightly bonded to the underying bone are all characterized by the excessive resorption of existing bone. Medical research has studied such conditions for some time, but problems have not yet been resolved and treatment methods remain only partially satisfactory.

Osteoporosis is generally associated with a reduced trabecular bone volume leading to increased risk of bone fractures. This process is probably due to a metabolic imbalance between the rates of new bone formation and bone resorption. Osteoporosis can be divided into two dasses: (1) type I or post-menopausal, which is related to reductions in estrogen content and affects primarily trabecular bone, and (2) type II or senile, which is related to reduced calcium absorption and affects primarily cortical bone.

Bone resorption can be divided into two processes which are probably being carried out concurrently. Phase I involves the inorganic metabolism conducted principally by osteoclasts, macrophages, monocytes, polymorphonudeocytes (PMNs), and fibroblasts. Osteodasts are multinucleated cells which reabsorb calcium from bone and cartilage. his process is regulated by parathyroid hormone (PTH), Pg-E.$_2$, and cAMP which activate lysosomal hydrolytic enzymes and causes solubilization of the minerals in the bone, releasing calcium to the blood. Phase II involves organic metabolism where there is proteolytic destruction of the bone matrix collagen, releasing hydroxyproline to the blood. This process is initiated by the release of collagenase and cathepsin D from osteoblasts at the bone surface. The cellular enzymes belong to the metalloproteinase group of proteolytic enzymes which usually function at neutral pH. PITH binds to membrane receptors on osteoblasts, pre-osteoblasts and osteocytes, which activates the release of calcium from the dense bone, probably due to the activation of lysosomal enzymes, e.g., cathepsins, CAMP, interleukin-1, or prostaglandins.

Estrogen, progesterone, testosterone and vitamin D3 levels decrease with age. With advanced age there is a reduction of calcitonin that severely reduces calcium absorption from the gut. There is a positive correlation between the extracellular reduction of these physiological parameters and with osteoporosis. Other factors are: smoking, lack of exercise, sunlight, and disease states like myeloma, skeletal metastasis, gastric surgery, anti-convulsant therapy, male hypogonadism, thyrotoxicosis, amenorrhea, anorexia nervosa, hyperprolactinanemia, diabetes mellitus, immobilization, osteogenic imperfecta, and homocystinuria.

Existing Treatments for Apatite Dissolution

Although a number of salts have been reported in certain experiments to counteract the dental decay process, no acceptable method of treatment using such salts, in the opinion of the inventor of the present invention, has been provided. One of the difficulties is providing a viable vehicle for delivering the salts. Still further, a number of safety issues are raised by some of the salts. Furthermore, sensory problems with respect to some of the salts prevent these salts from being taken on a regular basis by a patient to provide prophylactic benefits.

U.S. Pat. No. 5,378,131 provides a composition and method for preventing, or reducing the risk of, dental caries. A chewing gum is provided that includes a therapeutically effective amount of calcium glycerophosphate.

Calcium glycerophosphate counteracts the decay process. It is believed to function by reducing dernineralization and/or increasing remineralization of tooth enamel. Chewing gum is an especially good delivery vehicle because it can deliver the ingredient over prolonged periods of time and can be conveniently used almost anywhere at anytime as opposed to a rinse or dentifrices. The method includes the step of adding to a sugar containing gum a sufficient amount of calcium glycerophosphate to offset the cariogenicity of the sugar present in the gum.

The apatite-forming-systems of U.S. Pat. No. 5,460,803, discussed previously, are described as useful in prevention and/or repair of dental weaknesses such as dental caries, exposed roots and dentin sensitivity.

Existing Treatments for Osteoporosis

A number of agents have been noted to attenuate loss of bone mass in elderly humans or to accelerate bone growth in the young, such as estrogens, insulin, fluorides, anabolic steroids, calcitonin, growth hormone, fibroblast growth factor, transforming growth factor, epidermoid growth factor, bone morphogenic protein (osteogenin), diphosphates, and oral calcium supplements, with varying degrees of success. See Rodan, G. A. (1995) Emerging therapies in osteoporosis, Annual Reports in Medicinal Chemistry, 29: 275–285. Most evidence indicates that massive intakes of calcium (1500–2000 mg/day) orally does not prevent bone loss in post-menopausal women. It is not dear what the mechanism of action of estrogen is in blocking bone resorption.

It is dear, however, that the activity of osteoblasts and osteoclasts is coordinated and regulated by a complex mechanism and is affected by a variety of hormones and prostaglandins. See Raisz et al., Ann. Rev. Physiol., 43:225 (1981); U.S. Pat. No. 4,921,697 which teaches that inhibition of prostaglandin production by IFN-gamma is a treatment for osteoporosis and other bone-resorption diseases.

It is known that very little control is possible over the duration and the concentration at which prostaglandins reach the bone cells. It is also known that systemic injection or infusion of prostaglandins is an alternative with significant drawbacks since the lungs efficiently remove prostaglandins from circulation. See W. Harvey and A. Bennett, "Prostaglandins in Bone Resorption" CRC Press, pp. 37 (1988).

Frost et al. in "Treatment of Osteoporosis by Manipulation of Coherent Bone Cell Populations," Clinical Orthopedics and Related Research, 143, 227 (1979) discloses a theoretical model that suggests it should be possible to synchronize the activity and metabolism of bone cells by administering bone cell activating agents first and then administering a bone resorption inhibiting agent. This proposed model assumes that bone formation inhibition does not take place, because no bone resorption inhibiting agent is administered during the bone formation phase of the bone remodeling unit. EPO App. No. 0 381296 teaches the use of a kit wherein a bone activating period or treatment regime is followed by a bone resorption inhibiting regime. Many examples of bone activating compounds are cited in this reference. See also U.S. Pat. No. 5,118,667.

Uses of Synthetic Apatite

Apatite preparations have been proposed for use as bone inductors (to induce bone formation) and osteoconductors (by acting as scaffolds to facilitate continuous progression of new bone formation). These apatite preparations are mostly of synthetic origin and distinct structurally and chemically from the biological calcium-phosphate crystals in bone. All of these apatites are not only chemically and structurally distinct from the apatite crystals of bone, especially in their short range order, size and reactivity, but in some cases, they contain varying amounts of amorphous calciumphosphate, that is, calcium-phosphate solids which are not crystalline at all. In other instances, the calcium-phosphates made synthetically also contain calcium salts other than apatite crystals such as calcium oxides.

Other uses of apatite are diverse. For example, U.S. Pat. No. 5,427,754 to Nagata et al. issued Jun. 27, 1995 describes the use of apatite as an adsorbent in chromatography. The kind of protein adsorbed on hydroxyapatite varies with the kind of crystal faces of the hydroxyapatite. It is, therefore, necessary to produce hydroxyapatite which possesses crystal faces befitting the particular kind of protein to be adsorbed.

U.S. Pat. No. 5,405,436 to Raab et al. issued Apr. 11, 1995 describes a process for preparation of a hydroxyapatite suitable as an abrasive tooth-cleaning substance.

Uses of Natural Apatite

Living organisms are also apatite-forming-systems. In recent years, interest has been shown in the osteoconductive properties of a physiologically formed hydroxyapatite substratum that is obtained from living organisms. Thus, U.S. Pat. No. 5,439,951 to Glimcher et al. issued Aug. 8, 1995 provides a process for isolating from the biologically, naturally formed crystals of bone a purified apatite that is substantially free of organic material. Another example is a porous hydroxyapatite substratum that is obtained after hydrothermal conversion of the calcium carbonate exoskeletal microstructure of the scleractinian reef-building corals, Porites and Goniopora. This hydroxyapatite is characterized by a relatively uniform network of interconnected channels and pores, similar to the mineralized inorganic supporting structure of living bone. Experimental evidence has established the osteoconductive properties of the porous substratum when it is implanted in orthotopic sites, and the material has been used experimentally in reconstructive operations, particularly craniofacial procedures, as an alternative to autogenous bone grafts. Bone forms in porous hydroxyapatite that has been implanted extraskeletally in non-human primates. The shape and configuration (hereinafter referred to as "the geometry") of the porous hydroxyapatite substratum can be a relevant factor in determining the osteoconductive potential of hydroxyapatite. U.S. Pat. 5,355,898 provides evidence that the geometry of a substratum can be critical for inducing bone growth.

No general conclusions can be drawn from these representative reports except that the need for materials which are useful in fixation of implants and in repair or replacement of hard tissue defects remains and that the materials now available do not solve the many problems associated with the treatment of these problems, due to many variables, including the properties of the materials as well as the ease with which they can be manufactured and utilized.

Other Hard Tissue Related Problems

Bone mass is decreased by treatment with the following drugs over a long period of time: glucocorticoids, thyroxine, heparin, cytotoxic drugs, retinoids [vit A], phorbol esters, Pg-E's, interleukin-1, endotoxins and PTH.

A number of dangerous and painful disabilities are caused by the excessive resorption of bone. For example, rheumatoid arthritis and periodontitis (both associated with erosive joint disease), osteoporosis, and the failure of prostheses to remain tightly bonded to the underlying bone are all characterized by the excessive resorption of existing bone. For a discussion of treatment methods, see Reports in Medicinal Chemistry 29: 275–285. Medical research has studied such conditions for some time, but problems have not yet been resolved and treatment methods remain only partially satisfactory.

OBJECTS AND ADVANTAGES

The present invention is directed to processes and products that satisfy the need to (1) mitigate the effects of hard tissues diseases; (2) provide apatite compositions suitable for a variety of uses. Embodiments of the present invention significantly mitigate the effects of many hard-tissue diseases by providing methods and compositions for strengthening apatite in teeth and in bones. One manifestation of the improved apatite is larger crystallite size. Larger crystallite size confers resistance to dissolution. An understanding of the inverse relationship between crystallite size and dissolution rate helps to predict the properties of apatite having a large crystallite size. The present invention is constituted, however, without limitation by a relationship between crystallite size and the dissolution rate of apatite.

An embodiment of the present invention significantly mitigates the effects of excessive bone resorption and spares the use of other drugs presently used for mitigation, by providing a method to form stronger bones.

Many forms and uses of apatite exist, and examples of both have been cited herein. The differences between the various forms may be subtle; nevertheless, each difference alters the suitability of the apatite for a given purpose. Use of apatite in chromatography for example, requires apatite which possesses crystal faces befitting the particular kind of protein to be adsorbed. The present invention provides methods for producing forms of apatite. The new forms of apatite provided by the present invention could be useful in the manufacture of abrasives such as tooth pastes, osteoconductors, bone inductors, chromatographic media, and remineralizing agents, particularly for dental lesions. The possible forms of apatite provided by the present invention is not limited to the examples, but may include other forms as the need arises.

SUMMARY OF THE INVENTION

The present invention provides a method of treating or preventing diseases of bone and teeth comprising the administration of certain xanthines to a person in need of such treatment.

The xanthine administered is a compound of the formula

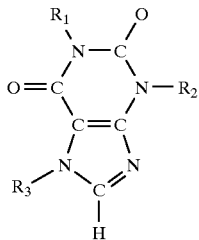

(formula I) wherein the $R_1$, $R_2$. and $R_3$ substituents are not all alkyl groups; and wherein an R substitutent is an alkyl group; a compound of this type is designated a "partially alkylated xanthine" for the purposes of this invention. Also, for the purposes of this invention, an alkyl group may comprise a short carbon chain, branched or unbranched, up to a carbon content of about about four atoms. Compounds of this class include theobromine (3,7-dimethylxanthine), paraxanthine (1,7-dimethylxanthine) and theophylline (1,3-dimethylxanthine).

The invention also comprises the use of partially alkylated xanthines, particularly the alkylated compounds of formula I for the production of apatite of high crystallite size.

The effect of methylation at $R_1$, $R_2$, and $R_3$ of formula I and of most combinations and permutations thereof have been tested by the present inventors. The inventors thus provide extensive guidance on the effect of the methyl substitutions and combinations and permutations of substitutions on the xanthine ring on apatite crystallinity. This guidance will enable one skilled in the art to identify additional alkylated xanthines with desirable effects on apatite crystallinity without undue experimentation. Nevertheless, when it is difficult to predict the exact effect of the alkylation in advance of doing so, one skilled in the art will appreciate that the effect will be evaluated by routine screening assays without undue experimentation. Such alkylated xanthines are commonly available. The Aldrich Chemical Co. catalog (Aldrich Chemical Co., Catalog handbook of fine chemicals, (1994–95), Aldrich Chemical Co., Inc. Milwaukee, WI) for example, lists many substituted xanthines that might have desirable effects on apatite crystallinity.

The present invention also encompasses a solvate, such as a hydrate, of a compound of formula (I) or a pharmaceutically acceptable salt thereof. The term "pharmaceutically acceptable salts" shall mean nontoxic salts of the compounds of this invention which are generally prepared by reacting the free base with a suitable organic or inorganic acid.

Preparation of Hydroxapatite with Large Crystallite Sizes.

The present invention provides an apatite-forming-system, comprising a solution containing solutes capable of forming apatite and an partially alkylated xanthine. An additional embodiment of the invention is a method for increasing the crystallite size of apatite by contacting an apatite-forming-system with an effective amount of an partially alkylated xanthine. An apatite-forming-system may comprise an in vitro system, such as a solution of mineral salts, or an in vivo system, such as an animal. An animal may form a steady-state in vivo system, or an in vivo system wherein the mass of the apatite increases. It is recognized that measurements of crystal or crystallite size using different techniques may produce different absolute values. For the purposes of this invention "crystallite size" refers to a relative measurement obtained by comparing matched samples of apatite, wherein one sample has been contacted with a test compound such as a xanthine, and the other has not, and everything else is equal.

Another embodiment of the present invention is an apatite, formed from an apatite-forming-system forming-system that is contacted with an partially alkylated xanthine. Another embodiment is an apatite formed from an apatite-forming-system that is contacted with an effective amount of a partially alkylated xanthine, wherein the crystallite size is increased relative to apatite formed from the apatite-forming-system that has not been contacted with an partially alkylated xanthine. Another embodiment of the present invention comprises processes for forming apatite by contacting an apatite-forming-system with an effective amount of a partially alkylated xanthine. The term "effective amount" shall mean that amount of a substance that will elicit the desired effect of an apatite-forming-system on crystals formed therefrom.

Another embodiment of the invention is a kit containing a therapeutic mixture comprising an effective amount of partially alkylated xanthine, sufficient to increase crystallite size of apatite when the partially alkylated xanthine is administered to an animal, and a pharmaceutically acceptable carrier. The term "pharmaceutically effective amount" shall mean that amount of a drug or pharmaceutical agent that will elicit the biological or medical response of a tissue, system or animal that is being sought by a physician or veterinarian.

The present invention also improves the crystallinity of teeth. The effect on teeth is surprising because the inventors have also shown that caffeine (1,3,7 trimethylxanthine) ingestion actually has a cariogenic effect. See Nakamoto, et al. (1993) Cariogenic effect of caffeine intake during lactation on first molars of newborn rats. Archs oral Biol. 38: 919–922; Falster et al. (1992) Physical examination of caffeine's effects on the enamel surface of first molar in new-born rats. Archs oral Biol 37: 111–118; Hashimoto, et. al. (1992) Effects of maternal caffeine intake during lactation on molar enamel surfaces in new-born rats. Archs oral Biol. 37: 105–109.

The invention includes, but is not limited to, the use of partially alkylated xanthines combined with any of the apatite-forming-systems and therapeutic methods cited herein.

Pharmaceutically Acceptable Embodiments

The chemistry, physical properties, production, use, occurrence, metabolism, toxicity, analysis and carcinogenicity of methylxanthines were reviewed by a working group of the International Agency for Research on Cancer (World Health Organization, Coffee, tea, mate, methylxanthines and methylglyoxal, IARC Monograph on the Evaluation of Carcinogenic Risks to Humans, Vol. 51 (1991).

It would be obvious to one skilled in the art to practice the present invention with the following pharmaceutically acceptable embodiments. Examples of pharmaceutically acceptable embodiments for treating osteoporosis are described in U.S. Pat. No. 5,409,911 to G. A. Rodan, issued Apr. 25, 1995. Examples of pharmaceutically acceptable embodiments of xanthines are provided in U.S. Pat. No. 5,409,934 to Smith et al. issued Apr. 15, 1995.

Suitable pharmaceutically acceptable salts are pharmaceutically acceptable base salts and pharmaceutically acceptable acid addition salts. Suitable pharmaceutically acceptable base salts of the compounds of formula (1) include base salts including metal salts, such as alkali metal salts for example sodium salts, or organic amine salts such as that provided with ethylenediamine.

Suitable acid addition salts of the compounds of formula (I) are the acid addition salts including pharmaceutically acceptable inorganic salts such as the sulphate, nitrate, phosphate, borate, hydrochloride and hydrobromide and pharmaceutically acceptable organic acid addition salts such as acetate, tartrate, maleate, citrate, succinate, benzoate, ascorbate, methanesulphonate, a-keto glutarate, a-glycerophosphate and glucose-1-phosphate. Preferably the acid addition salt is a hydrochloride salt.

The present invention also encompasses a solvate, such as a hydrate, of a compound of formula (I) or a pharmaceutically acceptable salt thereof.

The pharmaceutically acceptable salts of the compounds of formula (I) are prepared using conventional procedures.

The pharmaceutically acceptable solvates of the compounds of formula (I) or the pharmaceutically acceptable solvates thereof are prepared using conventional procedures.

The compounds of formula (I) are preferably in pharmaceutically acceptable form. By pharmaceutically acceptable form is meant, inter alia, of a pharmaceutically acceptable level of purity excluding normal pharmaceutical additives such as diluents and carriers, and including no material considered toxic at normal dosage levels. A pharmaceutically acceptable level of purity will generally be at least 50% excluding normal pharmaceutical additives, preferably 75%, more preferably 90% and still more preferably 95%.

A compound of formula (I) or where appropriate a pharmaceutically acceptable salt thereof and/or a pharmaceutically acceptable solvate thereof, may be administered per se or, preferably, as a pharmaceutical composition also comprising a pharmaceutically acceptable carrier.

Accordingly, the present invention provides a pharmaceutical composition comprising a compound of formula (I) or where appropriate a pharmaceutically acceptable salt thereof and/or a pharmaceutically acceptable solvate thereof, and a pharmaceutically acceptable carrier.

The active compound may be formulated for administration by any suitable route, the preferred route depending upon the disorder for which treatment is required, and is preferably in unit dosage form or in a form that a human patient may administer to himself in a single dosage. Advantageously, the composition is suitable for oral, aural rectal, topical, parenteral, intravenous or intramuscular administration or through the respiratory tract. Preparations may be designed to give slow release of the active ingredient The compositions of the invention may be in the form of tablets, capsules, sachets, vials, powders, granules, lozenges, suppositories, reconstitutable powders, or liquid preparations such as oral or sterile parenteral solutions or suspensions. Topical formulations are also envisaged where appropriate.

In order to obtain consistency of administration it is preferred that a composition of the invention is in the form of a unit dose.

Unit dose presentation forms for oral administration may be tablets and capsules and may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate; disintegrants, for example starch, polyvinylpyrrolidone, sodium starch glycollate or microcrystalline cellulose; or pharmaceutically acceptable wetting agents such as sodium lauryl sulphate.

The solid oral compositions may be prepared by conventional methods of blending, filling, tabletting or the like. Repeated blending operations may be used to distribute the active agent throughout those compositions employing large quantities of fillers.

Such operations are of course conventional in the art. The tablets may be coated according to methods well known in normal pharmaceutical practice, in particular with an enteric coating.

Oral liquid preparations may be in the form of, for example, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethylcellulose, aluminium stearate gel, hydrogenated edible fats; emulsifying agents, for example lecithin, sorbitan monooleate, or acacia; non-aqueous vehicles (which may include edible oils), for example almond oil, fractionated coconut oil, oily esters such as esters of glycerine, propylene glycol, or ethyl alcohol; preservatives, for example methyl or propyl p-hydroxybenzoate or sorbic acid; and if desired conventional flavouring or colouring agents.

Compositions may also suitably be presented for administration to the respiratory tract as a snuff or an aerosol or solution for a nebulizer, or as a microfine powder for insufflation, alone or in combination with an inert carrier such as lactose. In such a case the particles of active compound suitably have diameters of less than 50 microns, such as from 0.1 to 50 microns, preferably less than 10 microns, for example from 1 to 10 microns, 1 to 5 microns or from 2 to 5 microns.

For parenteral administration, fluid unit dosage forms are prepared utilizing the compound and a sterile vehicle, and, depending on the concentration used, can be either suspended or dissolved in the vehicle. In preparing solutions the compound can be dissolved in water for injection and filter sterilized before filling into a suitable vial or ampoule and sealing.

Additives such as a local anaesthetic, a preservative and buffering agents can be dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

The compositions may contain from 0.1% to 99% by weight, preferably from 10–60% by weight, of the active material, depending on the method of administration.

Compounds of formula (I), or if appropriate a pharmaceutically acceptable salt thereof and/ or a pharmaceutically acceptable solvate thereof, may also be administered as a topical formulation in combination with conventional topical excipients.

Topical formulations may be presented as, for instance, ointments, creams or lotions, impregnated dressings, gels, gel sticks, spray and aerosols, and may contain appropriate conventional additives such as preservatives, solvents to assist drug penetration and emollients in ointments and creams. The formulations may contain compatible conventional carriers, such as cream or ointment bases and ethanol or oleyl alcohol for lotions.

Suitable cream, lotion, gel, stick, ointment, spray or aerosol formulations that may be used for compounds of formula (I) or if appropriate a pharmaceutically acceptable salt thereof, are conventional formulations well known in the art, for example, as described in standard text books of pharmaceutics and cosmetics, such as Harry's Cosmeticology published by Leonard Hill Books, Remington's Pharmaceutical Sciences, and the British and US Pharmacopoeias.

Suitably, the compound of formula (1), or if appropriate a pharmaceutically acceptable salt thereof, will comprise from about 0.5 to 20% by weight of the formulation, favourably from about 1 to 10%, for example 2 to 5%.

DOSAGE

The dose of the compound used in the treatment of the invention will vary in the usual way with the seriousness of the disorders, the weight of the sufferer, and the relative efficacy of the compound. However, as a general guide suitable unit doses may be 0.1 to 1000 mg such as 0.5 to 200, 0.5 to 100 or 0.5 to 10 mg for example 0.5, 1,2,3, 4 or 5 mg; and such unit doses may be administered more than once a day, for example 2,3,4,5 or 6 times a day, but preferably 1 or 2 times per day, so that the total daily dosage for a 70 kg adult is in the range of about 0.1 to 1000 mg that is in the range of about 0.001 to 20 mg/kg/day, such as 0.007 to 3, 0.007 to 1.4, 0.007 to 0.14 or 0.01 to 0.5 mg/kg/day, for example 0.01, 0.02, 0.04, 0.05, 0.06, 0.08, 0.1 or 0.2 mg/kg/day; and such therapy may extend for a number of weeks or months.

The present invention describes a product comprising least one pharmaceutically acceptable active partially alkylated xanthine in a mixture of a tri-ester and polyvinylpyrrolidone, and a process for producing the same. In further embodiments, the present invention also relates to a process for encapsulating the composition within soft gelatin shells. The resulting compositions and capsules provide an effective means for oral delivery of a wide variety of pharmaceutically acceptable actives.

HUMAN AND VETERINARY USES

When used herein the term pharmaceutically acceptable encompasses materials suitable for both human and veterinary use.

TOXICOLOGY

For an extensive review of the toxicology of methylxanthines see Tarka, S. M. (1982) CRC Critical Reviews in Toxicology 9: 275–312. Cocoa is a major source of theobromine, where it is present in a concentration of approximately 1.89%. Tarka's critical review of the toxicology literature of methylxanthines demonstrates that cocoa per se has no reported adverse effects that would be injurious to man. According to Tarka, Zoumas and Gans (Short-term effects of graded levels of theobromine in laboratory rodents; Toxicol. and Applied Pharmacol. 49: 127–149 (1979), a diet containing a toxic level of theobromine (0.6% theobromine) provided the mature male rat with a theobromine intake of 310 mg/kg/day. This corresponds to a daily intake of approximately 18 g of theobromine for a 65 kg human. This level intake could be attained by the daily ingestion of approximately 171 1-oz bars of milk chocolate, assuming approximately 105 mg of theobromine/bar. Estimates of theobromine content of a 1-oz milk chocolate bar range from approximately 45 to 105 mg (Zoumas, B. L., Kreiser, W. R., and Martin, R. A. Theobromine and caffeine content of chocolate products J. Food Sci. 45: 314–316 (1980); Tarka, Zoumas and Gans (Short-term effects of graded levels of theobromine in laboratory rodents; Toxicol. and Applied Pharmacol. 49: 127–149 (1979)). Plasma half-life of theobromine in humans is about six hours (Resman, B. H., Blumenthal, H. P., and Jusko, W. J. Breast Milk distribution of theobromine from chocolate. J. Pediat. 91: 477–480 (1977); Drouilard, D. D., Vesell, E. S., and Dvorchick, B. N. Studies on theobromine disposition in normal subjects. Clin. Pharmacol. Ther. 23: 296–302 (1978). In rats, the half life of theobromine in plasma is about three hours (Welch, R. M., Hsu, S. Y., and DeAngeles, R. L. Effect of araclor 1254, phenobarbitol and polycyclic aromatic hydrocarbons on the plasma clearance of caffeine in the rat. Clin. Pharmacol. Ther. 22: 791–798 (1977)). Thus, to attain a toxic level of theobromine, a 65 kg human would be required to eat about 86 1-oz milk chocolate bars/ day.

Theophylline is used in the treatment of respiratory diseases. The mechanisms of action of methylxanthine uses, dosage recommendations and target plasma levels in the neonate are reviewed by O'Donnell J. Theophylline misadventures: Part I. Neonatal Netw 1994 Mar; 13(2): 3543. See also Paterson J W. Lulich K M. Goldie R G., Pharmacology of asthma treatment: an overview. (1995) Med J Aust; 162(1): 42-3.

NUTRITIONAL SUPPLEMENT

Nutritional supplements for combatting conditions associated with bone-related diseases are known. Such a supplement, which for the purposes of the claims of the present application are regarded as pharmaceutical compositions, is in the form of a topically administrable composition, e.g. a cream, gel or ointment, a parenterally administrable composition, e.g. an aqueous solution, or an orally administrable composition, e.g. tablets or capsules and, particularly, orally administrable compositions in which the partially alkylated xanthine is provided with a gastric juice resistant release delaying coating. Thus in one preferred embodiment of the invention the pharmaceutical composition of the invention takes the form of a nutritional supplement.

Such nutritional supplements, which most preferably are sterile, may be in a form adapted for enteral, parenteral or topical administration, but most preferably will be in a form adapted for oral ingestion. The nutritional supplement may take the form of dietary supplement, such as a foodstuff. The nutritional supplement may alternatively be in a conventional pharmaceutical dosage form adapted for administration to the gastrointestinal tract.

In this regard, forms such as tablets, coated tablets, capsules, powders, drops, suspensions, solutions, syrups and suppositories deserve particular mention. Nevertheless as partially alkylated xanthine nutritional supplementation may be achieved by parenteral or topical administration, for example by injection or by topical application (e.g. of an ointment, lotion, cream, paste or gel or the like), or by transdermal iontophoretic delivery, the nutritional supplement may be in the form of a composition adapted for one of these administration modes.

Where the nutritional supplement is prepared in a conventional pharmaceutical dosage form it may of course also contain conventional pharmaceutical carriers or excipients.

For oral administration, the nutritional supplement may conveniently take the form of a foodstuff, for example a food or drink mix, into which a partially alkylated xanthine is incorporated. The nutritional supplement may particularly suitably be in the form of a so-called "complete" foodstuff, analogous to those which are prepared to serve as the major or sole source of nutrition for example for people wishing to loose weight, for post-operative patients, for elderly patients, for convalescents, or for individuals with specific dietary needs (e.g. patients with diabetes, coeliac disease or cystic fibrosis). For most people, however, a partially alkylated xanthine supplemented foodstuff will preferably be of a type that is ingested daily in similar quantities, and for this reason the supplement will particularly conveniently comprise the partially alkylated xanthine and a cereal or legume foodstuffs base. The nutritional supplement may take the form of a partially alkylated xanthine containing multivitamin/multi-mineral preparation, for example in the form of tablets, capsules, or drops, especially enteric coated tablets or capsules. In this regard, compositions are especially preferred which contain the partially alkylated xanthines together with sources of one, some or all of the vitamins and the other essential elements. In another embodiment, the partially alkylated xanthines may be incorporated into an enteral alimentation solution. The nutritional supplement may, however, contain the partially alkylated xanthines as the only active ingredients.

For topical administration, the nutritional supplement will again preferably be in a form adapted for regular application in substantially similar quantities and thus the partially alkylated xanthines may particularly conveniently be incorporated within cosmetics, such as facial creams and ointments and the like.

The partially methylated xanthine content in the nutritional supplement will be selected according to the nature of the supplement and its administration route but in general will be within the range 1 mg/ 100 g body weight. This amount is comparable to consumption of one to seven 1-oz milk chocolate bars by a 65 kg human. Any effective concentration, however, is satisfactory as long as unwanted side facts are tolerable.

Thus, for example in complete foods which might be administered in a dose of 500 g/day, a partially alkylated xanthine content of 50 to 1000 mg might be contemplated.

Such nutritional supplements may be used to combat a wide range of conditions associated with essential chemical deficiency, in particular conditions which appear to be associated with diseases of the hard tissue, and the uses and methods of the invention are deemed to relate to the treatment of such conditions as well as the conditions mentioned earlier herein.

The compositions of the invention may of course contain further ingredients, such as for example conventional pharmaceutical or topical disinfectant formulation aids, e.g. emulsifiers, extenders, flavours, colouring agents, surfactants, pH adjusting agents, ointment bases, geling agents, propellants, stabilizers and the like. The compositions may also contain other physiologically active agents.

DETAILED DESCRIPTION OF THE INVENTION

Figure 1:
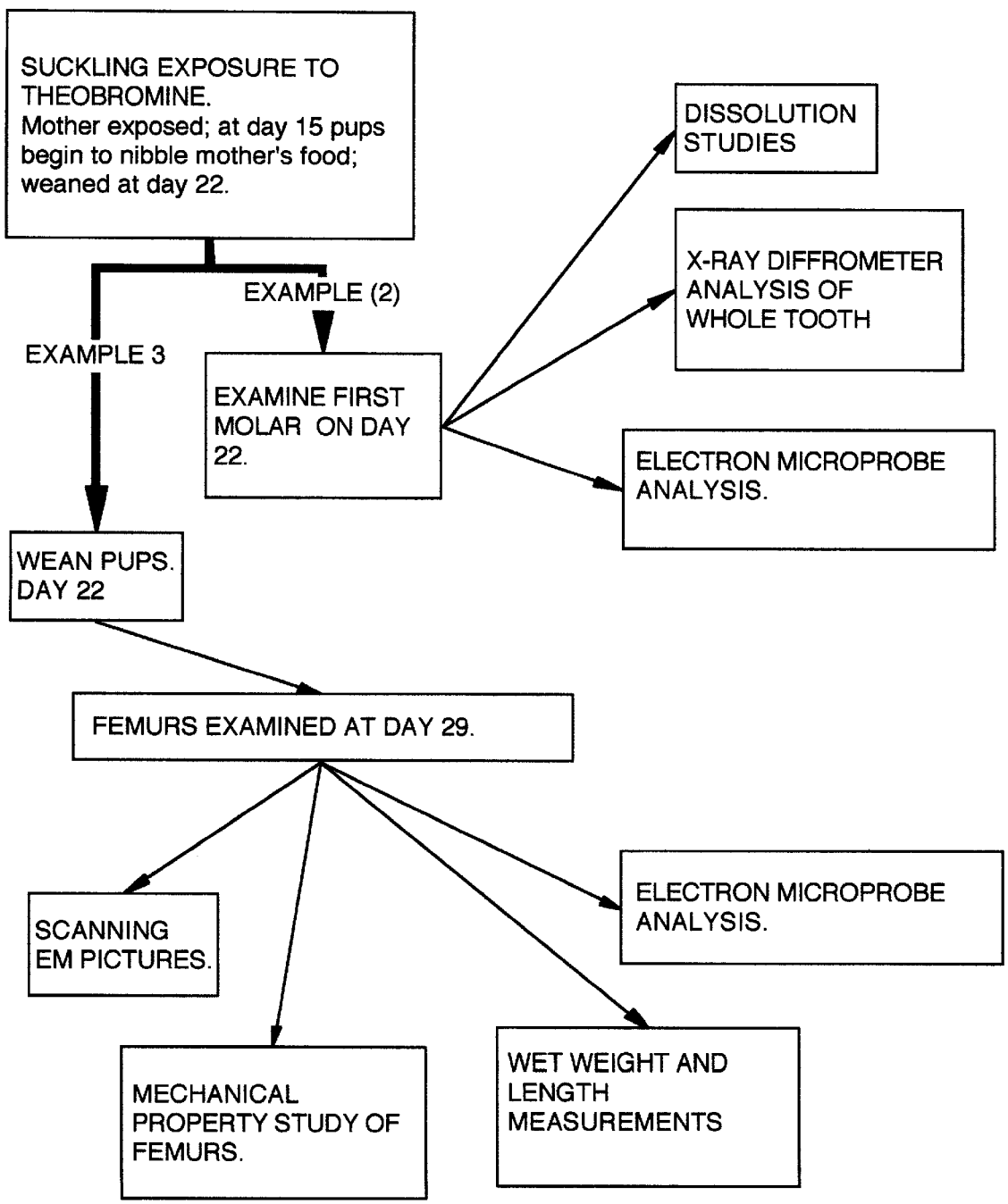
FIG. 1. Flow chart depicting the experimental plan for investigation of in vivo effects of theobromine on apatite.

In the following experiments, the present inventors have demonstrated the effects of partially alkylated xanthines on 4 apatite-forming-systems, one in vitro and three in vivo.

The apatite-forming-systems and parameters examined include (1) crystallite size of apatite crystallized from dilute salt solution; (2) dissolution rates, crystallite size, and chemical composition of apatite formed in the first molars of suckling (22 day) rats; (3) mechanical strength, electron micrographs, and chemical composition of femurs from 29 day rats; (4) crystallite size of bone apatite formed in ovariectomized rats (69 days).

It is evident from the attached results that methylxanthines, except caffeine, enhance crystallinity of apatite grown in vitro. In vivo, our results indicate that theobromine also enhances crystallinity, mechanical strength, and dissolution resistance of apatite. Our results do not indicate a more intense mineralization of either bone or tooth material. Evidently, no additional apatite material is deposited in either bones or teeth, but the crystallite size is increased in animals exposed to theobromine, making the apatite less easily dissolved. Application of these compounds may have profound effects on the health of human bone and teeth.

The present unique discovery may have application in combating bone and dental disease by taking the proper amount of these methylxanthines at the appropriate time. Our present discovery of methylxanthines' role in calcification is unique and could lead to an enormous commercial advantage for various types of industry. The amount of theobromine added to the diet in the present study was minute, and this is a further advantage of these methylxanthines.

From these experimental results, it will be apparent to one of ordinary skill in the art that many changes and modifications can be made thereto without departing from the spirit or scope of the appended claims. More specifically, it will be apparent to one of ordinary skill in the art that partially alkylated xanthines may be used to modify any apatite-forming-system, including but not limited to, those described herein.

The development and use of the ovariectomized rat model is described by Kalu, D. N. (1991) (The ovariectomized rat model of postmenopausal bone loss. Bone and Mineral, 15: 175–192).

The age of the animals chosen for an experiment is a significant factor in the model. In general, young animals exhibit more turnover in bone structure, and thus the effects of any drugs administered tends to be faster and higher when young animals are used.

Having now generally described the present invention, the same will be more readily understood through reference to the following examples which are provided by way of illustration, and are not intended to be limiting of the present invention.

EXAMPLE 1
In Vitro Studies

In vitro experiments of growing apatite from dilute solutions of $CaCl_2$ and $Na_3PO_4$ were performed.

All solutions contained 0.01 molar $CaCl_2$ and $NA_3PO_4$. Several sets of experiments were performed with the addition of each of the methylxanthines or uric acid at two concentrations, 50 mg and 200 mg/liter. The effect of the xanthine compounds was compared with a control solution containing $CaCl_2$ and $Na_3PO_4$ only.

Solutions were mixed at 25° C. and the pH adjusted to 9–9.5 with 0.1 molar NaOH and left to crystallize for 20 days. The crystalline precipitate was washed 5 times with distilled water and prepared for X-ray diffraction which was performed on a "SCINTAG XDS 2000"™ X-ray diffractometer. The instrument was operated at 40 kV potential and 20 mA current. Scans were performed using step scan mode with 0.02 step increments and 3 seconds dwell time. The (300) reflection was scanned to investigate crystallinity.

The following results in terms of FWHM (full width-half maximum peak height) divided by maximum peak height (FWHM/M) and for the (300) reflection is given in Table 1 for the control and the xanthine compounds.

TABLE 1

X-Ray diffraction analysis of apatite grown from solution

| Amount of additive/liter solution | FWHM/M | ÔFWHM/M |
|---|---|---|
| Control | 0.75 | 0.00 |
| Caffeine, 200 mg | 1.00 | −0.25 |
| Caffeine, 50 mg | 0.90 | −0.15 |
| Uric Acid, 200 mg | 0.96 | −0.21 |
| Uric Acid, 50 mg | 0.90 | −0.15 |
| Theobromine, 200 mg | 0.15 | 0.60 |
| Theobromine, 50 mg | 0.19 | 0.56 |
| Theophylline, 200 mg | 0.40 | 0.35 |
| Theophylline, 50 mg | 0.50 | 0.25 |
| 1-methylxanthine, 200 mg | 0.60 | 0.15 |
| 1-methylxanthine, 50 mg | 0.68 | 0.07 |
| 3-methylxanthine, 200 mg | 0.21 | 0.54 |
| 3-methylxanthine, 50 mg | 0.39 | 0.36 |
| 7-methylxanthine, 200 mg | 0.45 | 0.30 |
| 7-methylxanthine, 50 mg | 0.68 | 0.07 |

Figure 3:
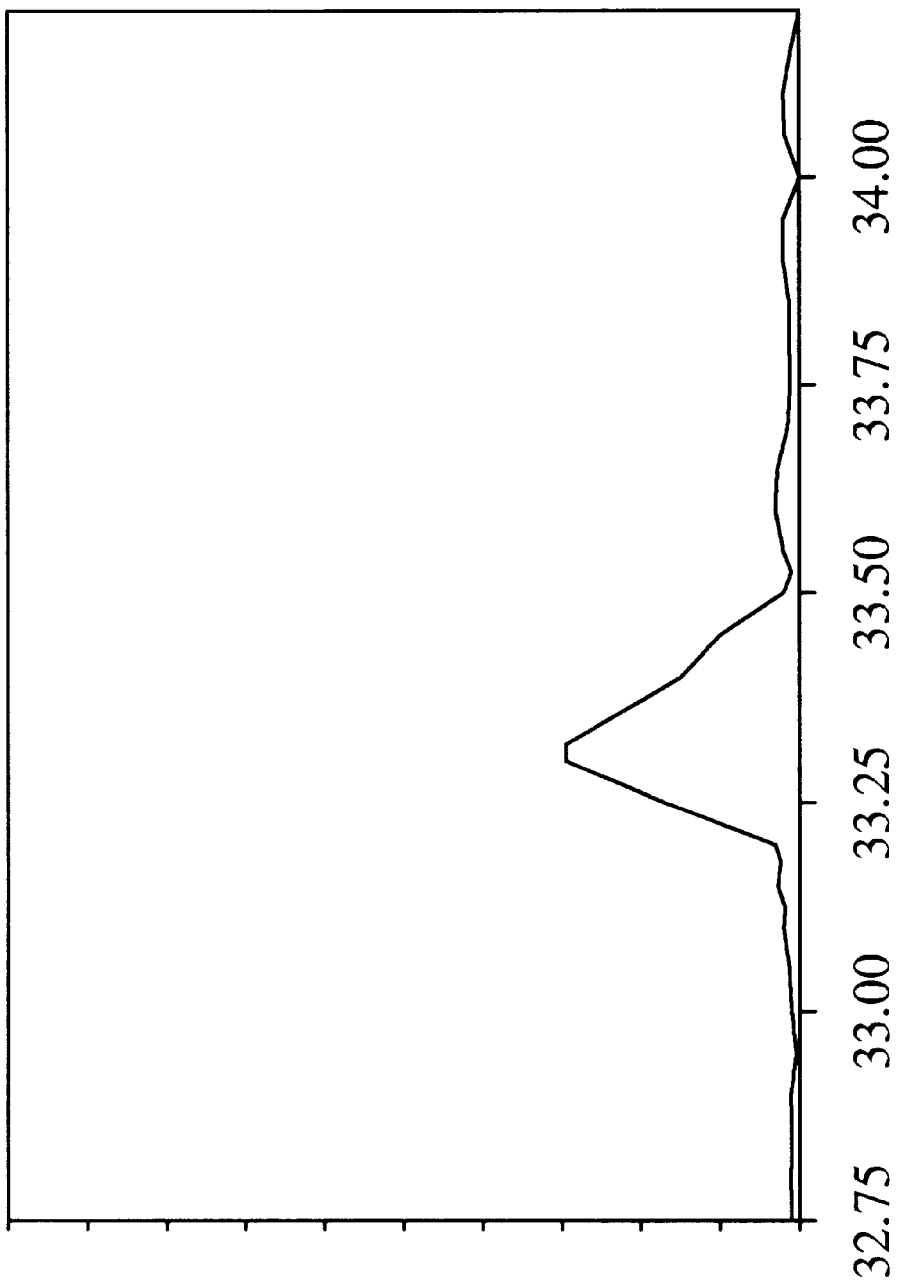
FIG. 3. X-ray diffraction scan of the (300) reflection of apatite grown in vitro without additives (control).
Figure 4A:
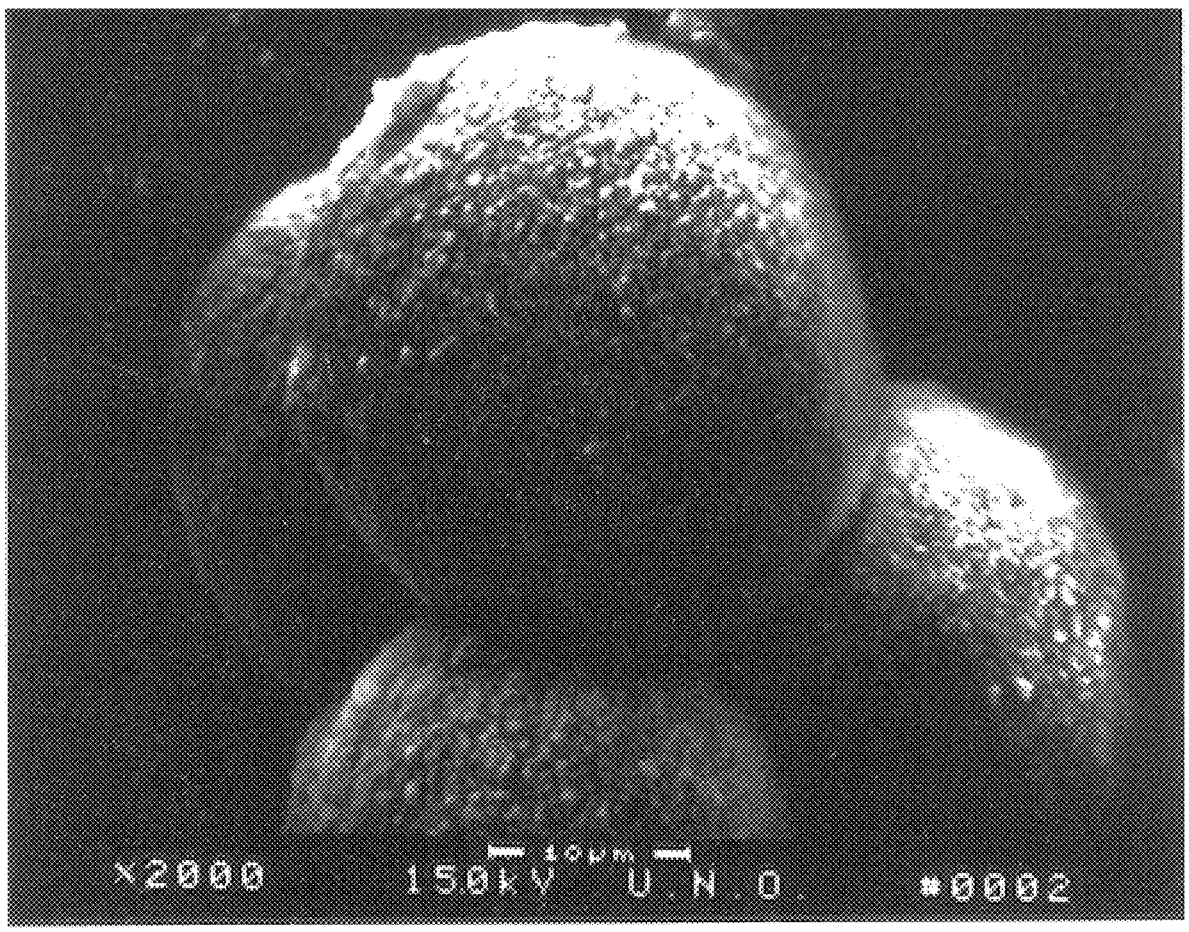
FIG. 4, A and B. Secondary electron images of apatite grown in vitro without additives (control). Arrow points at a crystallite measuring 0.5 microns.
Figure 4B:
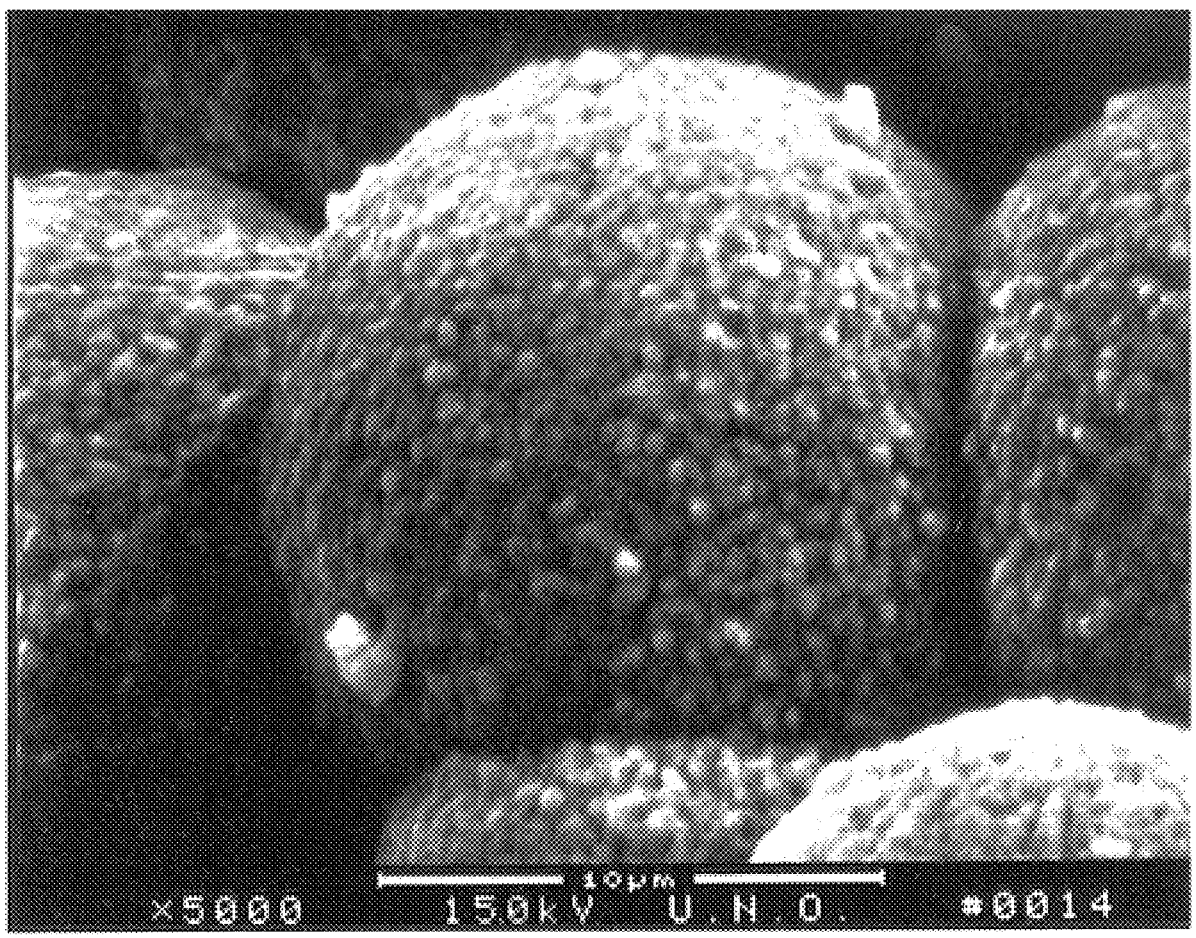
Figure 5:
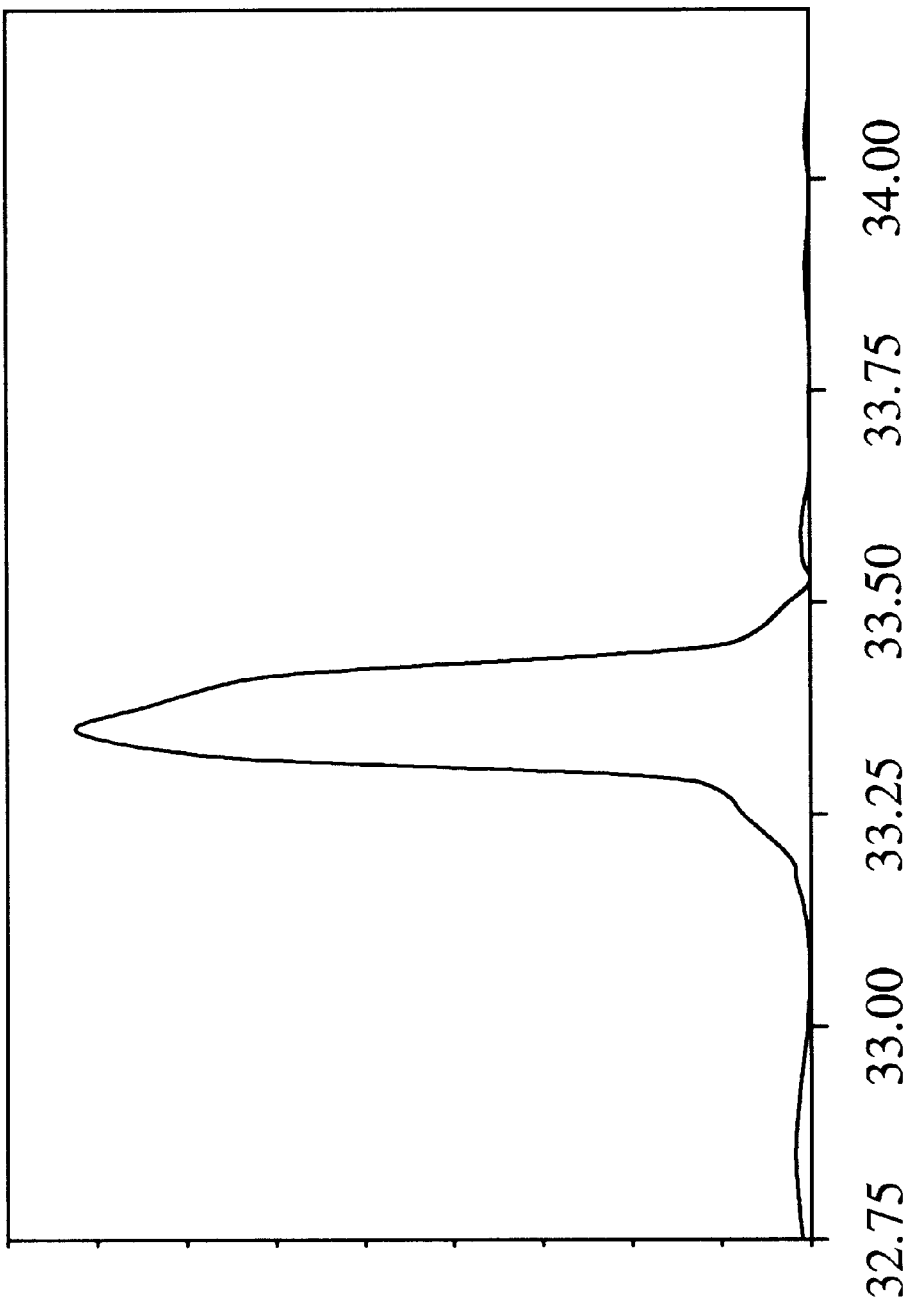
FIG. 5. X-ray diffraction scan of the (300) reflection of apatite grown in vitro in presence of 200 mg theobromine/liter.
Figure 6A:
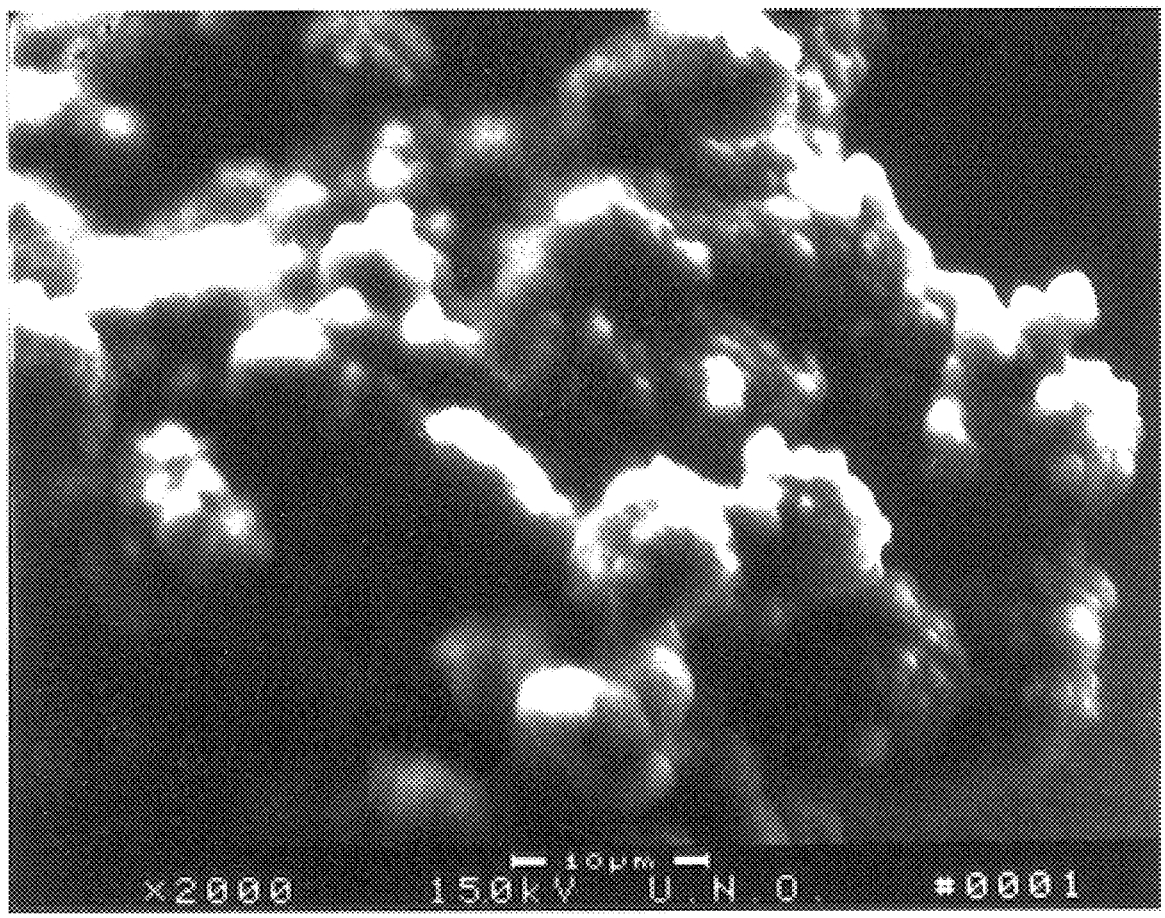
FIG. 6, A and B. Secondary electron images of apatite grown in vitro in presence of 200 mg theobromine/liter. Arrow points at a crystallite or a cluster of crystallites measuring over 2 microns.
Figure 6B:
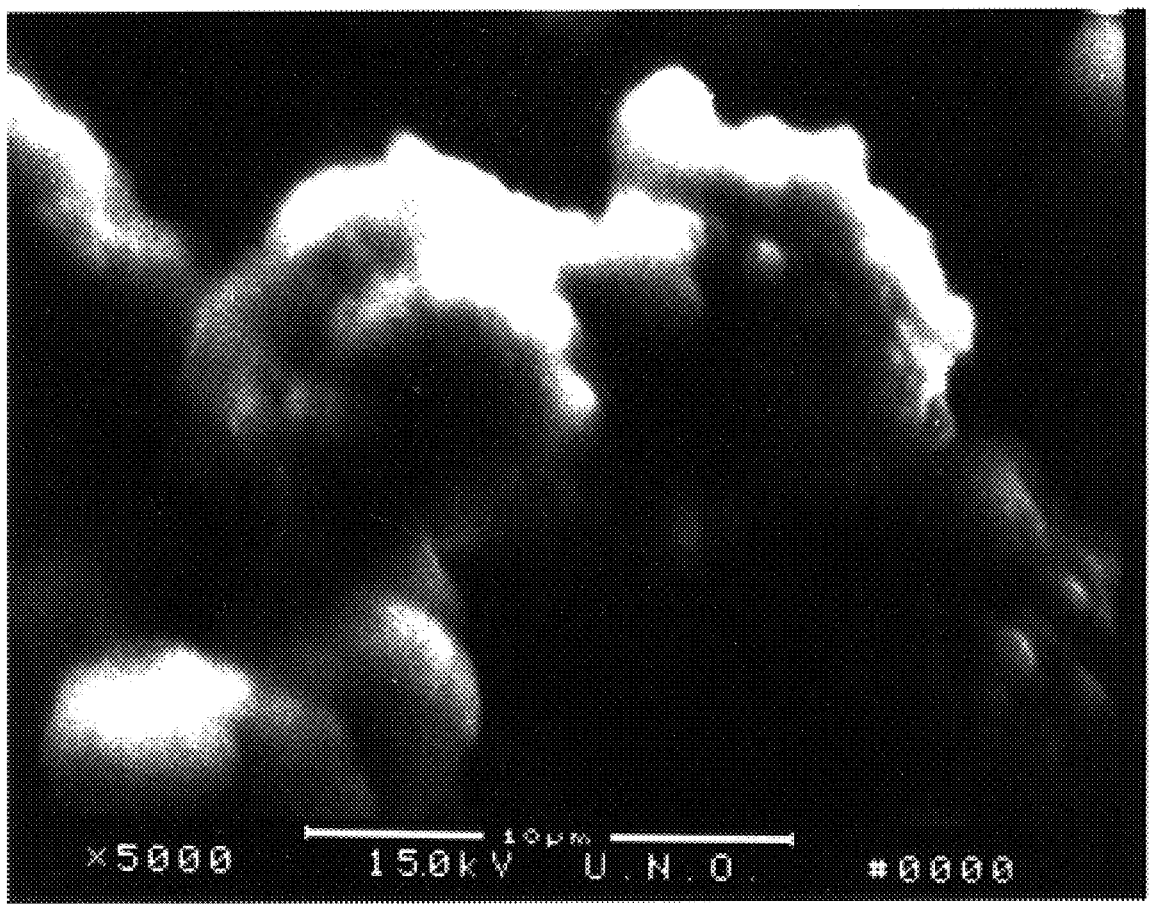
Figure 7:
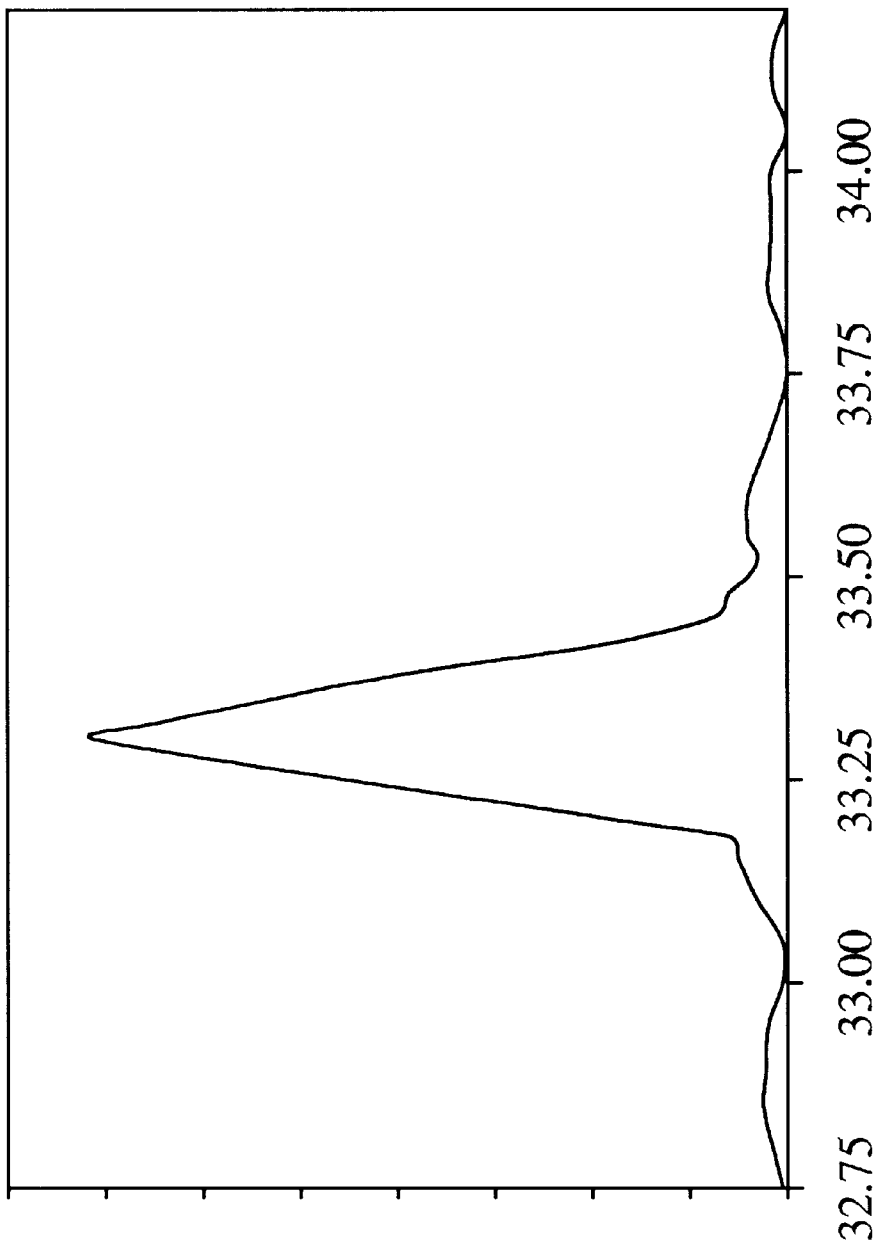
FIG. 7. X-ray diffraction scan of the (300) reflection of apatite grown in vitro in presence of 50 mg theobromine/liter.
Figure 8A:
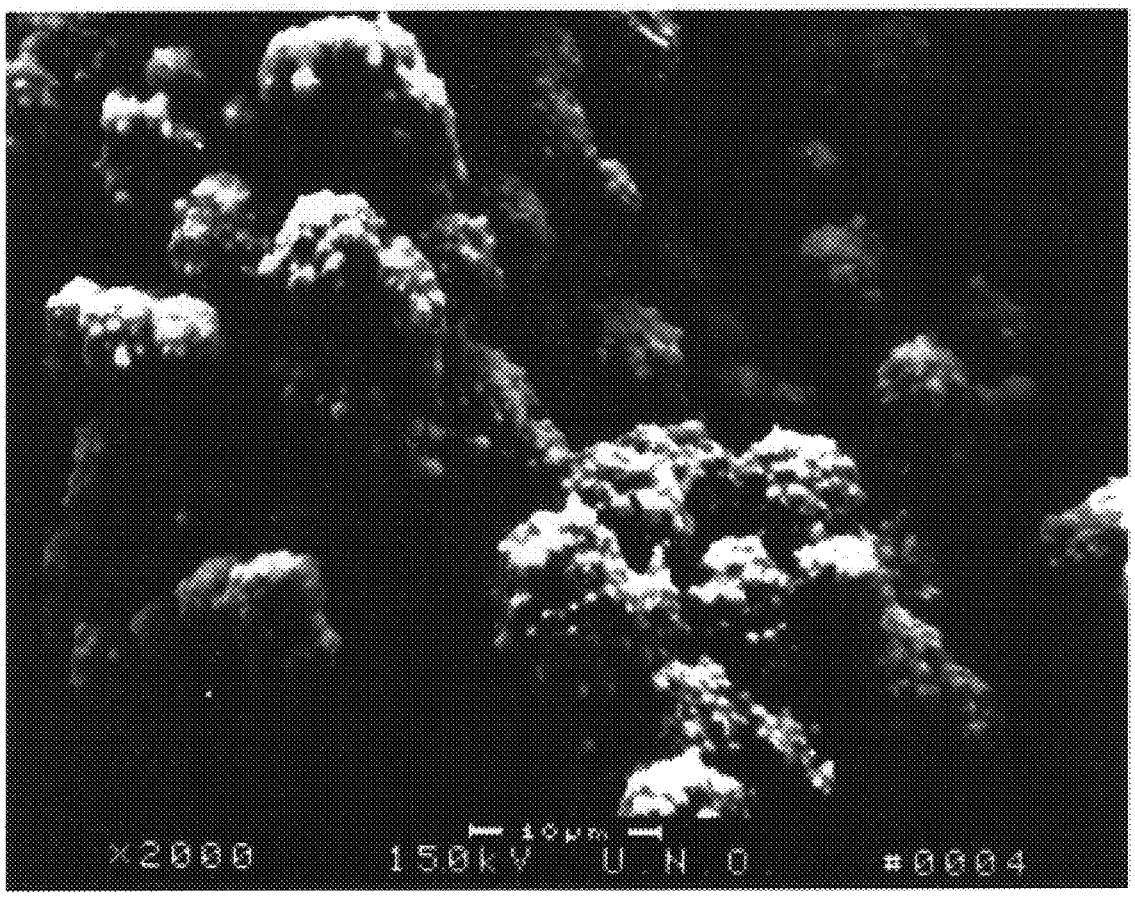
FIG. 8, A and B. Secondary electron images of apatite grown in vitro in presence of 200 mg 3-methylxanthine/liter. Arrow points at a crystallite or a cluster of crystallites measuring approximately 1 micron.
Figure 8B:
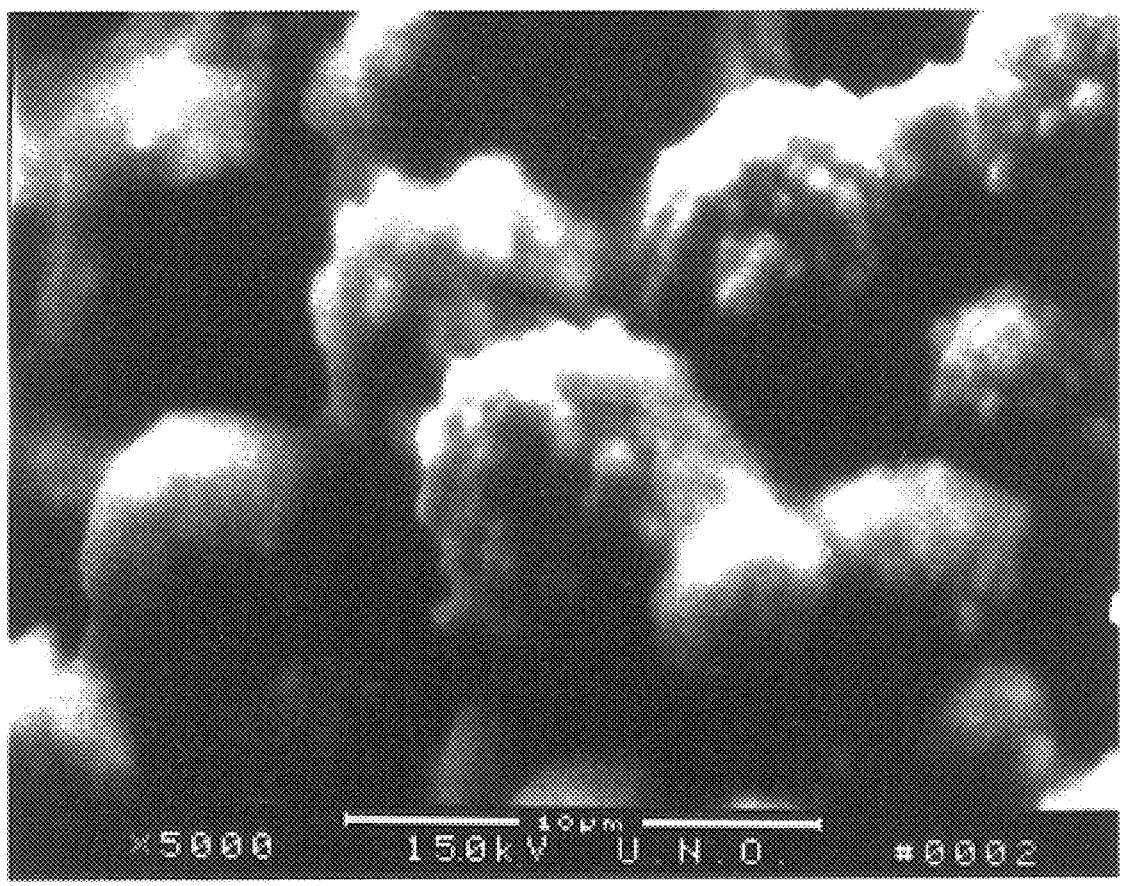

From the data, it appears that the experiments run with theobromine (FIGS. 5, 6, & 7) or 3-methyl xanthine (FIG. 8) show the most pronounced increases in crystallinity, compated to controls (FIGS. 3 & 4). This is evident from lower values of the ratios FWHM/M compared to the control (Table 1). Lower values of this ratio indicate better crystallinity. All of the methylated xanthines, except caffeine, increased the crystallinity of the precipitating apatite. In every case, the crystallinity increased with xanthine concentration. Caffeine and uric acid decreased the cystallinity of the apatite, also in a dose-dependent manner.

In Vivo Experiments

The overall plan of examples 2, 3, and 4 is depicted in FIG. 1.

EXAMPLE 2
Studies of First Molars From Day 22 Rats

Timed pregnant Sprague-Dawley rats were purchased from the breeder (Holtzman strain). They were maintained on a 12 hour light/ dark cycle and fed laboratory chow and water ad lib. At term, litters delivered within an 8 h period were combined and designated as day 1; eight pups were randomly assigned to each dam. Then, the dams with the recombined litters were divided into two groups. Dams from group 1 (N=8) were fed a 20% protein diet. Those from group 2 (N=8) were fed a 20% protein diet supplemented with theobromine. The composition of the 20% protein diet is casein, 200 g; dextrose, 191 g; sucrose, 178 g; dextrin, 192 g; mazola corn oil, 150 ml; mineral mix ("Rogers-Harper Mineral Mix"™), 40 g; choline chloride 50% (w/ v), 4 ml; cellulose, 35 g; and vitamin mix ("AIN Vitamin Mixture 76"™), 10 g. The theobromine supplementation was 1 mg/100 of the dam's body weight until weaning at day 22, and 1 mg/100 g of the offspring's body weight after weaning. We adjusted the theobromine supplement in the maternal and offspring's diets based upon their weight and food intake in order to maintain a constant ratio of theobromine (1 mg/100 g body weight). Theobromine supplementation in the diet was followed in exactly the same way as caffeine supplementation in the diet in out previous studies (see Nakamoto, T. and Shaye, R. Protein-energy malnutrition in rats during pregnancy modifies the effect of caffeine on fetal bones. J. Nutr. 116:633–640, 1986). The amount of theobromine supplemented to the maternal diet corresponded to approximately 8.8 mg/100 g diet or 0.0088% for days 1–14; for days 14–22, it was 5.9 mg/100 g diet or 0.0059%. After weaning, theobromine added to the offspring's diet was 8.9 mg/100 g diet or 0.0089% for days 22–29. The theobromine intake by the dams during lactation and the growing period of the offspring per day was comparable to approximately one to seven 1-oz milk chocolate bar by a 65 kg human, after adjustment for size and pharmacokinetics (Tarka, S. M., Zoumas, B. L. and Gans, J. H. Short-term effects of graded levels of theobromine in laboratory rodents. Toxicol. Appl. Pharmcol. 49:127–149, 1979). Note that the intake of theobromine by the suckling offspring was much lower than that of the dams, since the only source of theobromine intake by the pups came from the dam's milk, at least up to day 15. From day 15 to day 22 the pups start nibbling the dam's food which contains theobromine.

The amount of theobromine that rats consumed in this experiment has an equivalent human consumption, in proportion to body weight and pharmacokinetic differences. For the most accurate estimate, the extrapolation should be adjusted either for the pharmacokinetics of theobromine metabolism (Resman, B. H., Blumenthal, H. P., and Jusko, W. J. Breast milk distribution of theobromine from chocolate. J. Pediat. 91: 477–480 (1977); Drouillard, D. D., Vesell, E. S., and Dvorchick, B. N. Studies on theobromine disposition in normal subjects. Clin. Pharmacol. Ther. 23: 296–302 (1978), or metabolic body size. In humans, the half life of theobromine in plasma is about 6 hours; in rats, it is about three hours (Welch, R. M., Hsu, S. Y., and DeAngeles, R. L. Effect of araclor 1254, phenobarbitol and polycyclic aromatic hydrocarbons on the plasma clearance of caffeine in the rat. Clin. Pharmacol. Ther. 22: 791–798). The amount of theobromine used in the current experiment (1 mg/100 g body weight) is equivalent to human dose of 650 mg/kg. Assuming that the theobromine content of a one oz. bar of milk chocolate is 45 to 105 mg as stated previously, approximate intake of theobromine becomes three to seven bars of one oz. milk chocolate, when extrapolated using pharmacokinetics of theobromine metabolism. When the conversion is based on the metabolic body weight ($kg^{0.75}$), (Kleiber, M. In: The fire of life, an introduction to animal energetics. New York Wiley andsons, p. 177–216 (1961)) the present dosage (1 mg/100 g body weight) in rats is equivalent to 129 mg/65 $kg^{0.75}$. This corresponds approximately to slightly more than one to three bars of one oz. milk chocolate for a 65 kg human.

Figure 2:
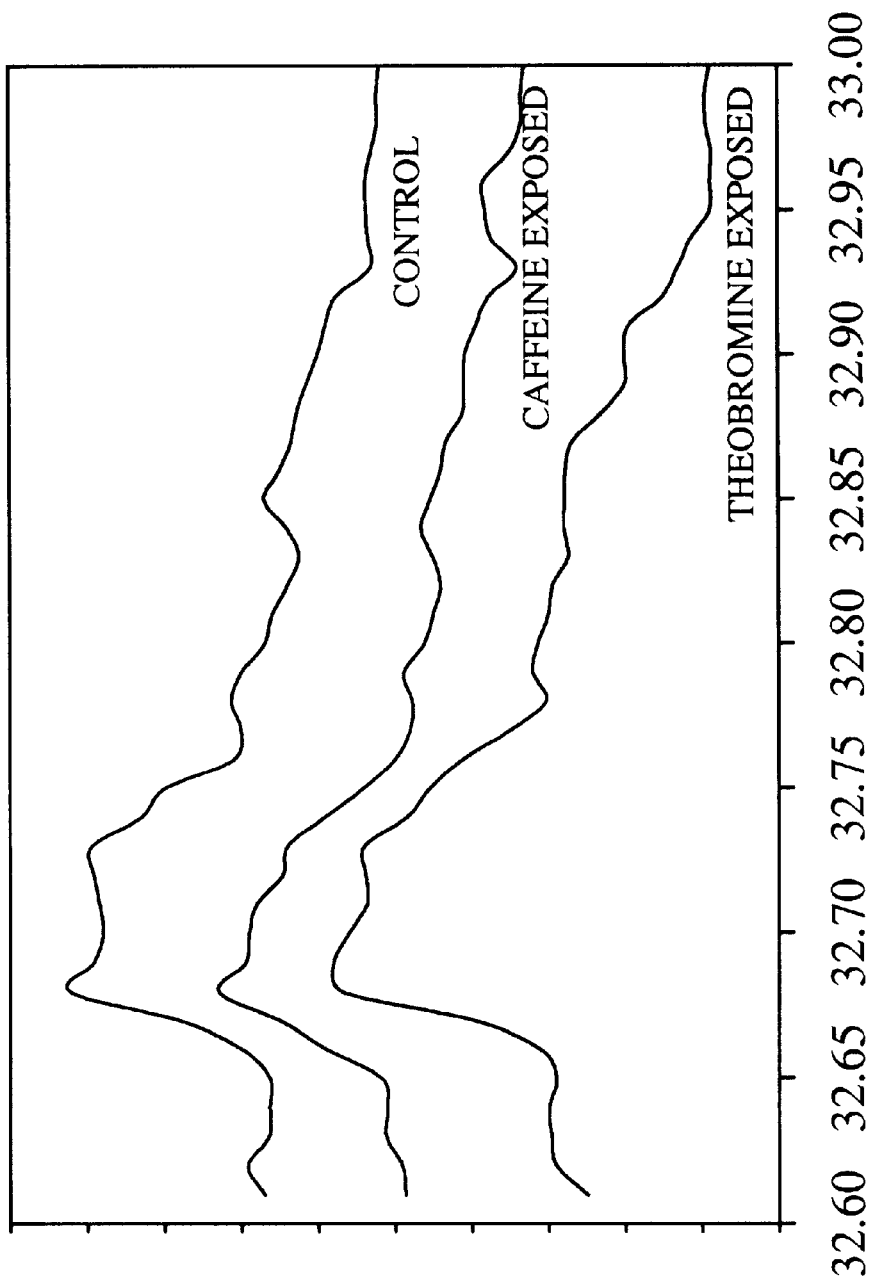
FIG. 2. X-ray diffraction scan of the (300) reflection of apatite from whole teeth extracted from 22 day rats exposed to caffeine, theobromine, or no methylxanthine. Control rat, upper tracing; theobromine exposed rat, lower tracing; caffeine exposed rat, middle tracing.
Figure 9:
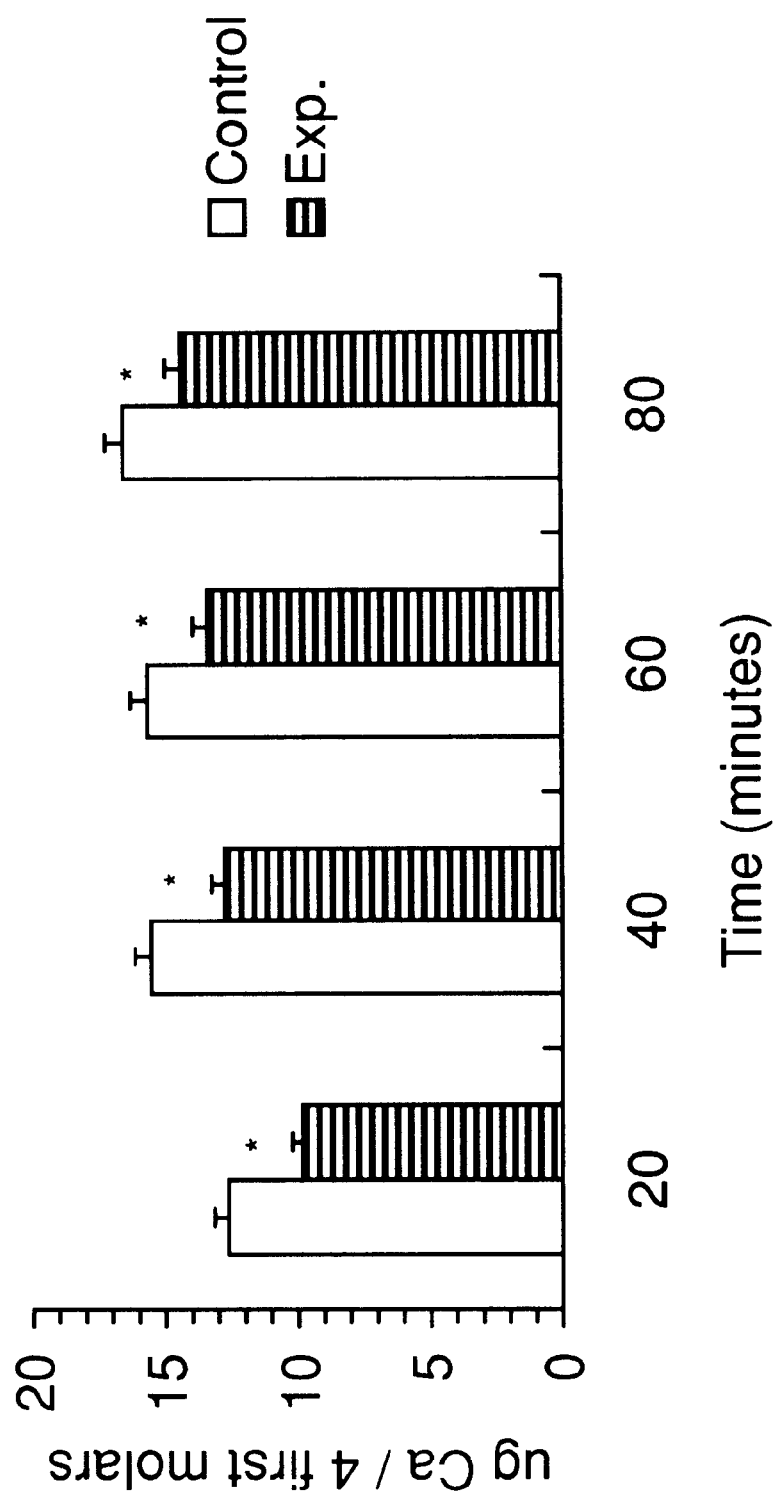
FIG. 9. Ca dissolved from first molars. *Significantly different from the control at $p<0.05$.
Figure 10:
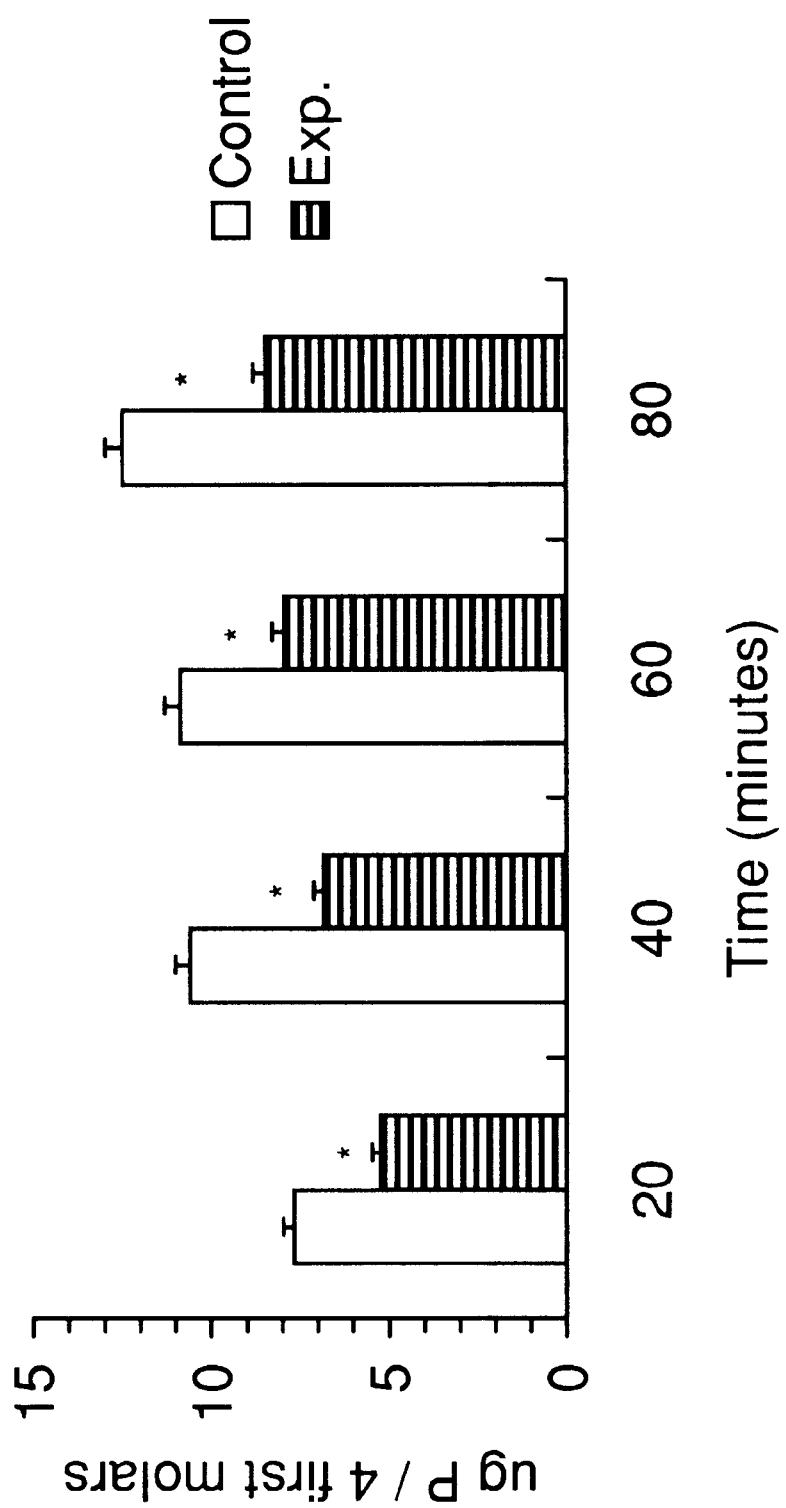
FIG. 10. $P_2O_5$ dissolved from first molars. Significantly different from the control at $p<0.05$.
Figure 11:
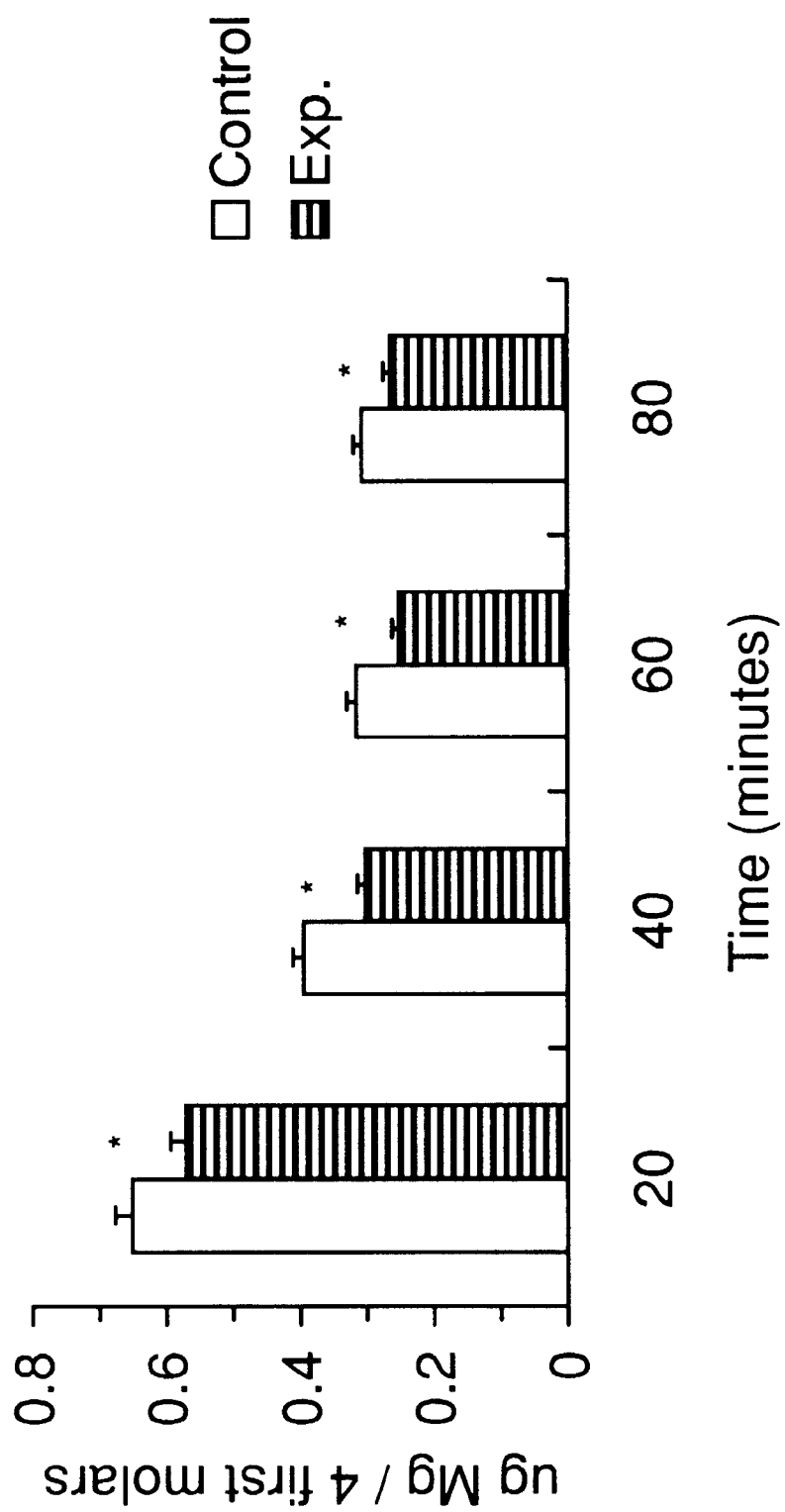
FIG. 11. Mg dissolved from first molars. *Significantly different from the control at $p<0.05$.

On day 22, maternal milk and blood were collected. Then randomly selected pups were killed; their blood was collected; and first molars of the mandible and maxilla were removed. Randomly selected first molars were mounted with a sticky wax on a small plastic block in order to study the acid solubility on the enamel. surface. First molars were examined later by electron microprobe analysis and X-ray diffractometry (FIG. 2). FIGS. 9–11 show the statistical significance between control and experimental groups of the minerals dissolved from 1st molars.

Calcium and phosphorus concentrations were determined in enamel of first molars extracted from theobromine exposed rats or control rats by an "ARL"™ electron microprobe analysis. The instrument was operated at an acceleration potential of 15 kV and a beam current of $1.0 \times 10^{-7}$ A. A fluorapatite from Cerro de Mercado, Mexico, was used as a standard. The results obtained are shown in Table 2.

X-ray diffractometry results depicted in FIG. 2 and other measurements show a consistent relationship of higher crystlinity, i. e. larger crystallites, in the whole first molars of animals exposed to theobromine, compared to the control group.

TABLE 2

Electron microprobe analyses of $P_2O_5$ and CaO content of enamel from first molars extracted from control and theobromine-exposed rats.

| Sample # | $P_2O_5$ weight percent | CaO weight percent |
|---|---|---|
| a) Control group | | |
| 28 | 38.11 | 53.24 |
| 30 | 36.68 | 53.60 |
| 10 | 36.55 | 52.20 |
| Average | 37.11 | 53.01 |
| b) Experimental group | | |
| 29 | 34.55 | 52.70 |
| 24 | 37.63 | 53.17 |
| 37 | 38.53 | 51.79 |
| Average | 36.90 | 52.55 |

From the data of Table 2, the overall contents of CaO and $P_2O_5$ appear comparable within the expected margin of error. This suggests that composition of crystallites of the enamel between control and experimental groups are the same.

EXAMPLE 3

Femurs at 29 Days

On day 29, the remaining offspring were killed, blood was collected, and the femur removed. Femurs were cleaned and dried overnight at 85° C. Crystalline phases in the femurs were examined by scanning electron microscopy. An "AMRAY 1820"™ digital scanning electron microscope was used in the study. The instrument was operated at an acceleration potential of 15 kV, a working distance of 18 mm, a 300 micron final aperture was used, and a spot size of 4.0 was employed in the study. Flat polished and etched (3 percent acetic acid, 20 seconds each time) cross sections of femur were investigated. It was noted that etching was generally more intense in the control group.

Figure 12:
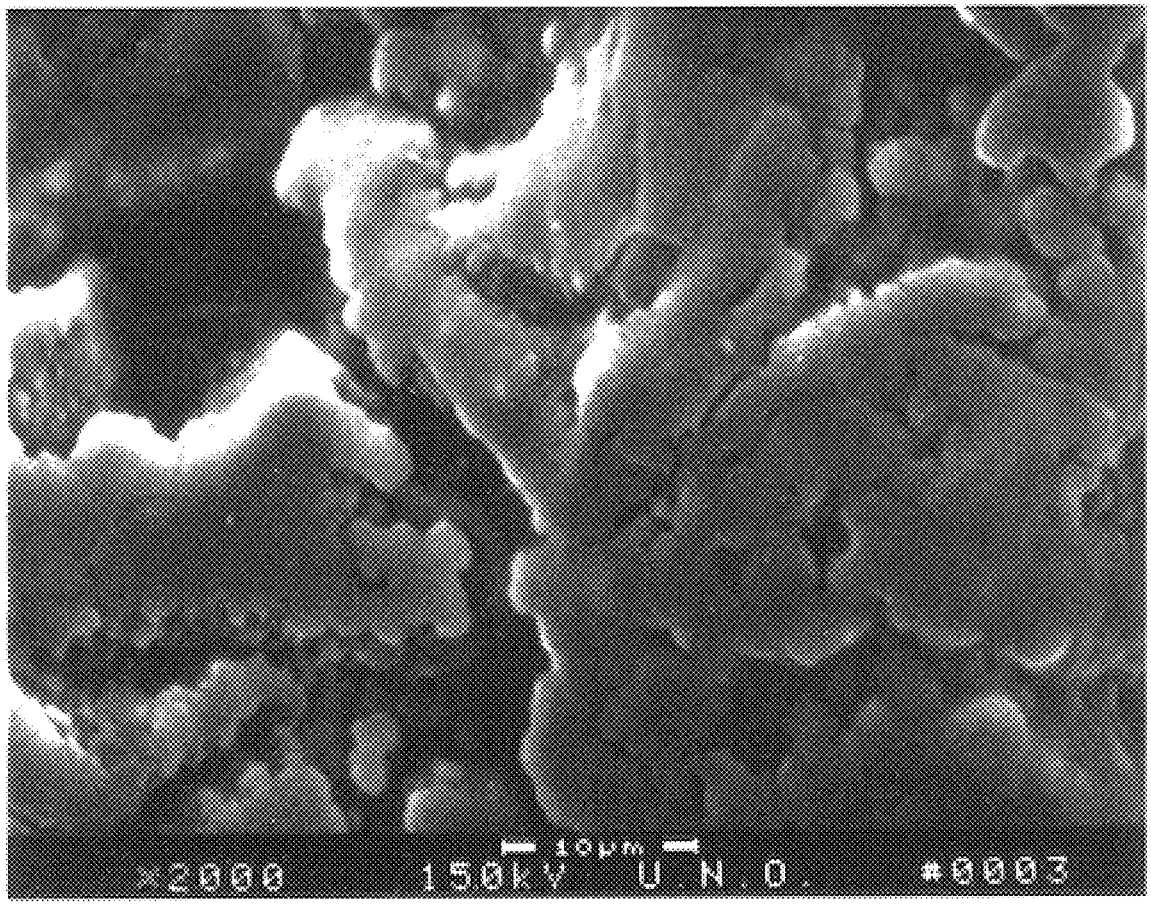
FIG. 12. Secondary electron image of female femur bone material which has been etched in acetic acid (experimental group).
Figure 13:
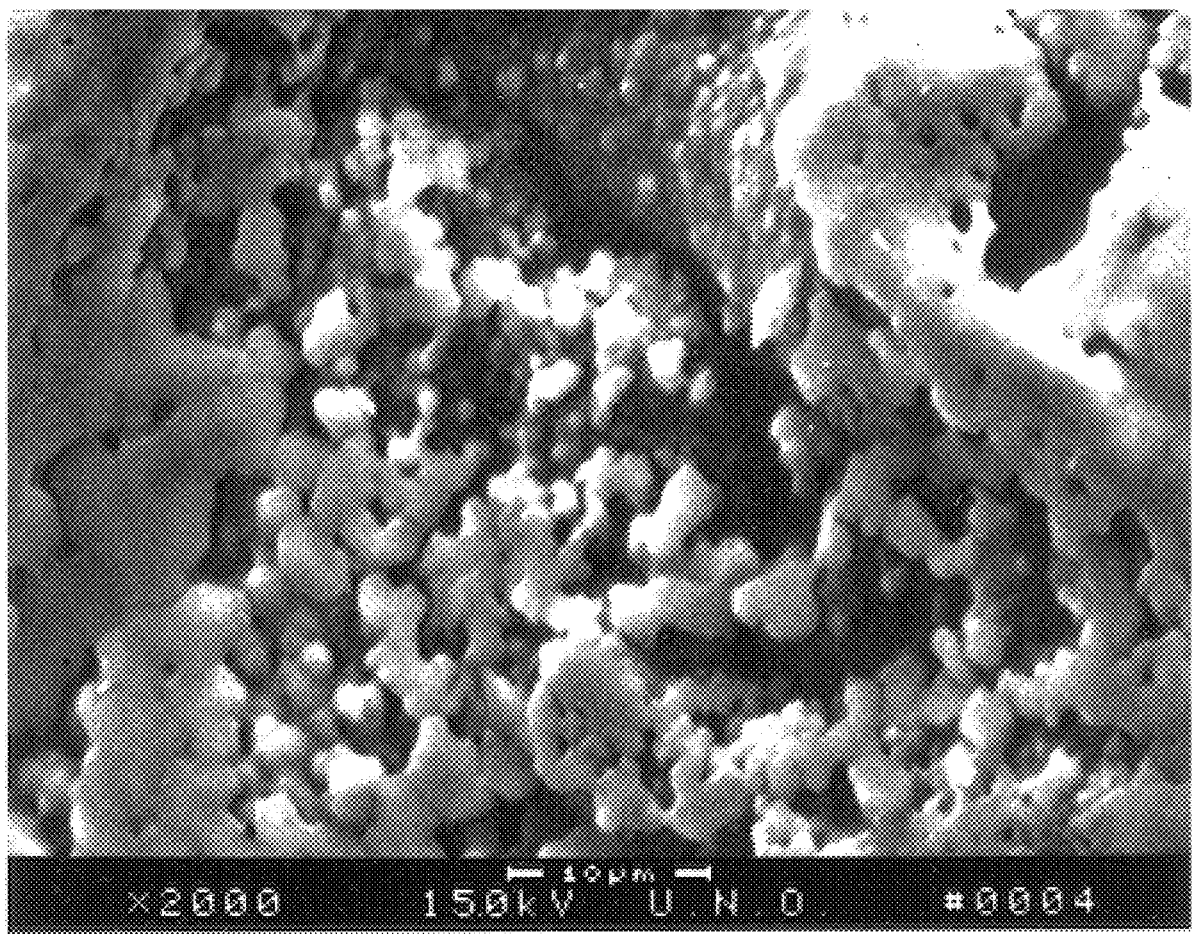
FIG. 13. Secondary electron image of female femur bone material which has been etched in acetic acid (control group).
Figure 14A:
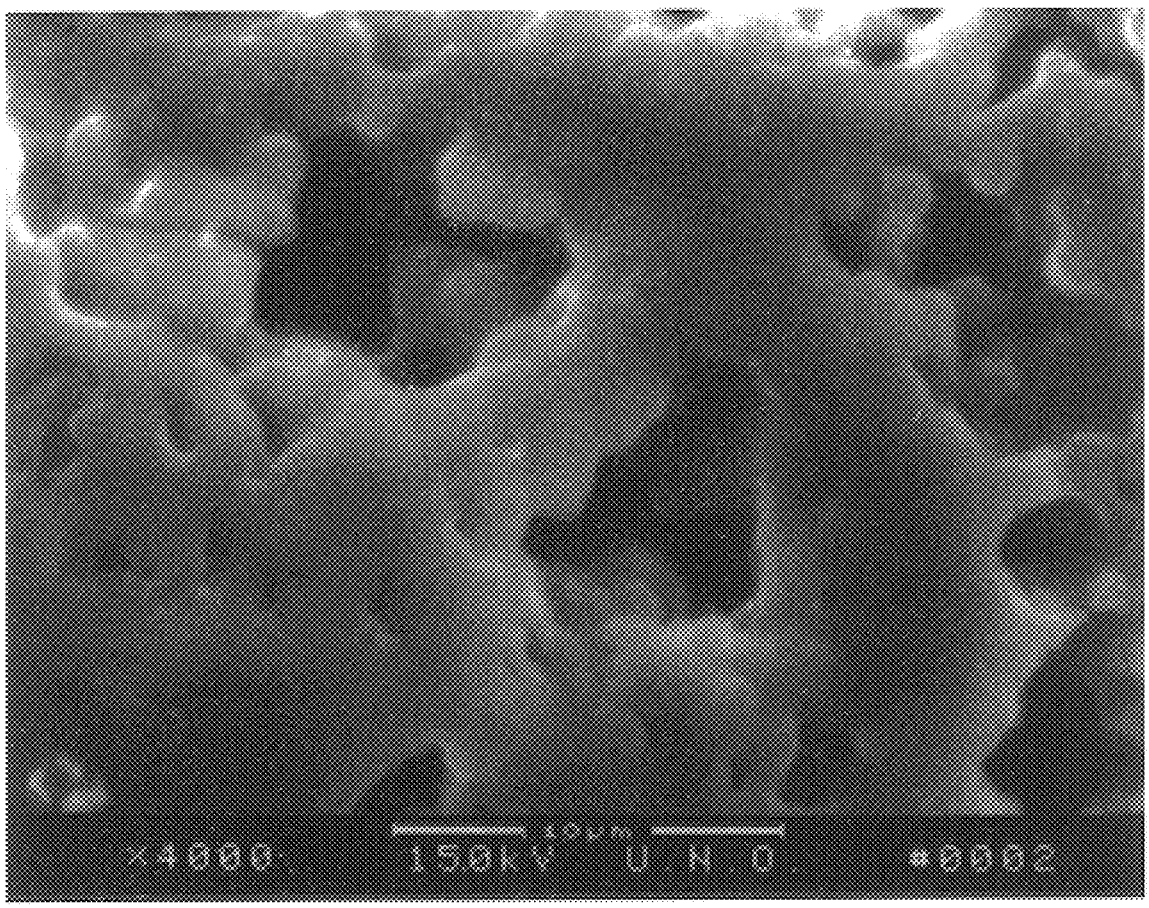
FIG. 14, A and B. Higher magnification of secondary electron image of the interior parts of femur. #0002: experimental group; #0000: control group.
Figure 14B:
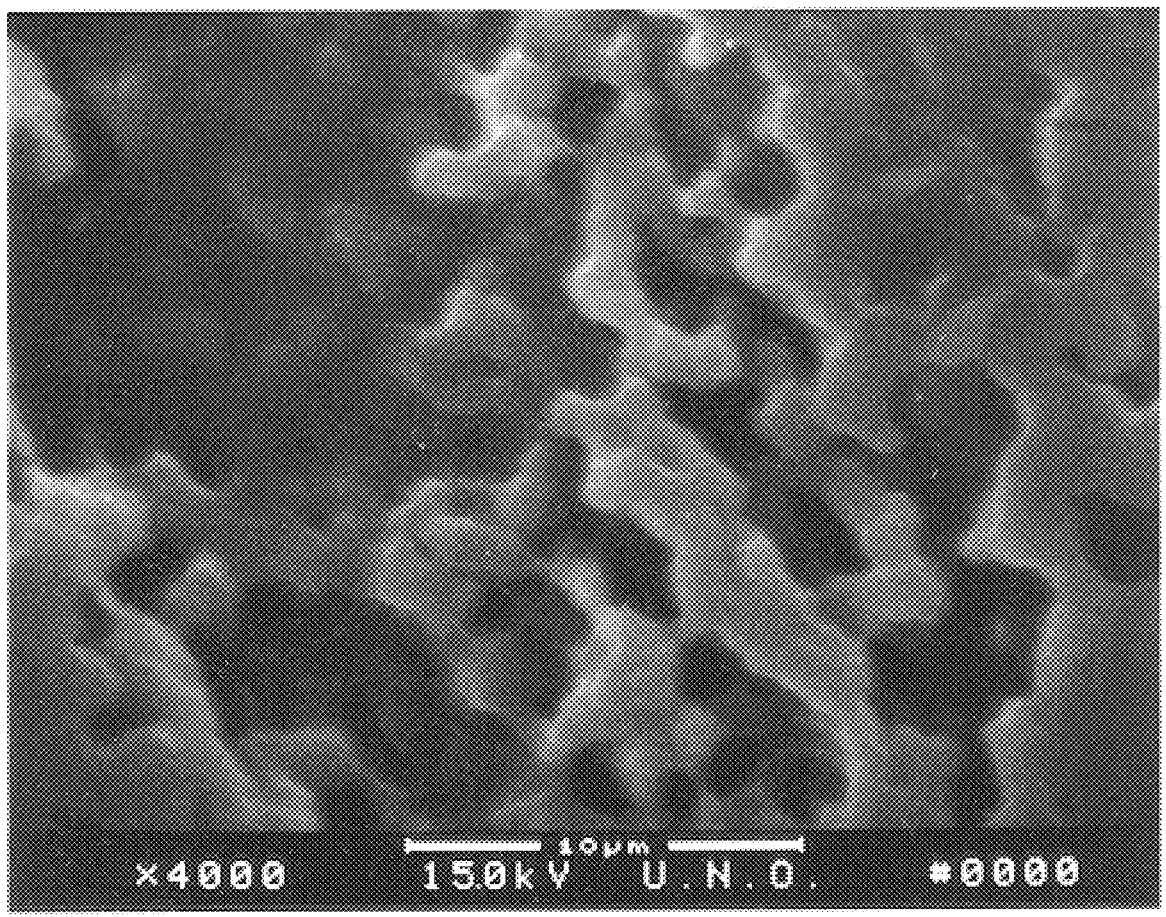

Remnant structures in the bone appeared coarser in the experimental group (FIG. 12) than in the control group (FIG. 13). Higher magnifications are shown (FIG. 14).

Figure 15:
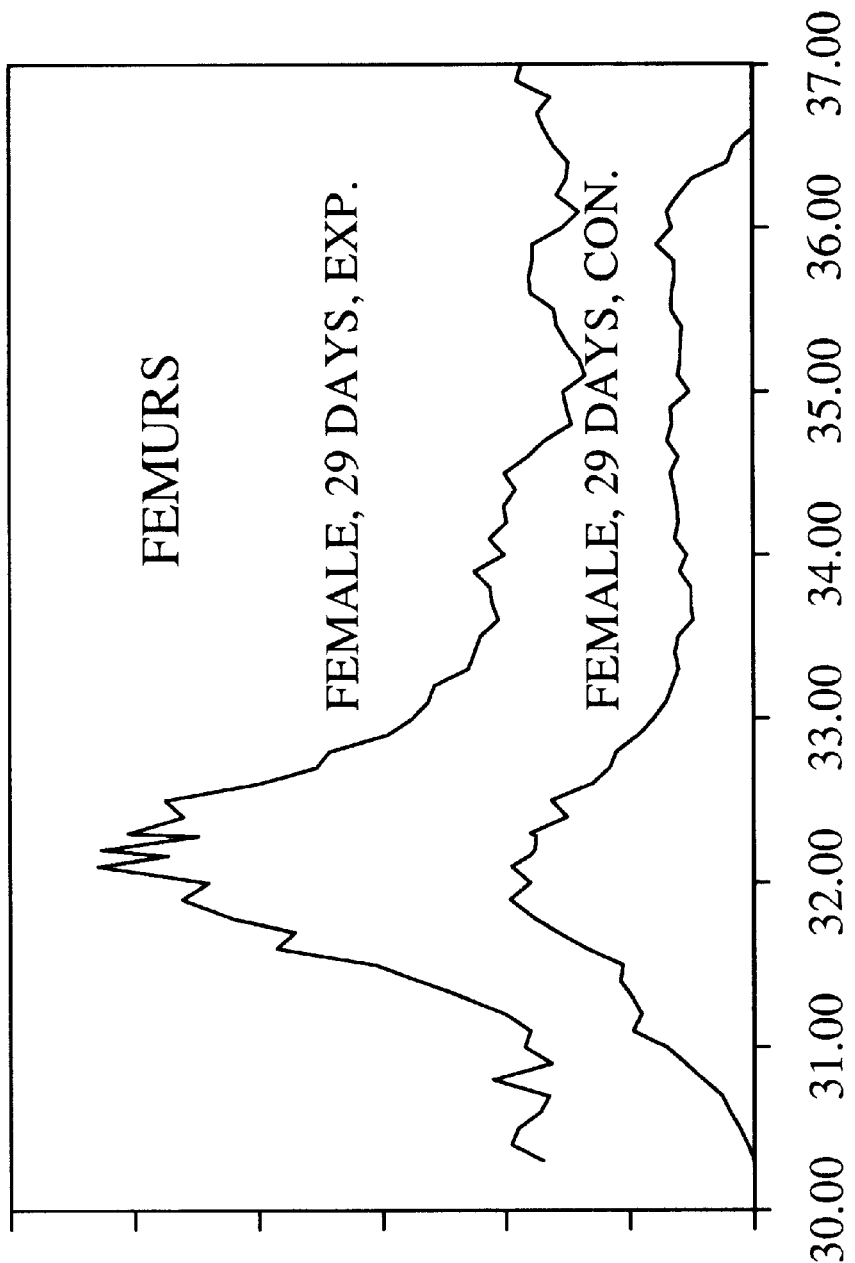
FIG. 15. X-ray diffraction scan of apatite obtained from the femur of a 29 day old female from the experimental group (upper tracing) and from the control group (lower tracing).

Femurs were removed, powdered and examined with a "SCINTAG XDS 2000"™ X-ray diffractometer. X-ray diffractometry (FIG. 15) of a female femur at 29 days showed larger crystallites in the experimental group than in the control. This figure illustrates the increased crystallinity, as shown by the smaller FWHM/M, of the experimental group relative to the control group.

X-ray diffraction procedures can be used to obtain information on crystallite-size of a sample within a limited range. A method of measuring this is to obtain measurements of reflection width/ reflection height ratios. This is typically referred to as the "Full width-half maximum" (FWHM) value, calculated by measuring the peak breadth at half the peak height. A sample of a crystalline compound with a crystallite or particle size of about $10^{-3}$ cm will produce the sharpest peaks with smallest "FWHM" values; whereas, a sample with a particle size of $10^{-6}$ cm will produce far broader, more diffuse peaks. Thus, if crystallite size of a material is a size range of approximately 0–1000 Ångstrøoms, it is possible to estimate or compare crystallite sizes of the material by measuring the FWHM values. The mathematical relationship is as follows:

$$B = 0.9 \, l/t \, \cos q$$

where B is the broadening of the diffraction line measured at half its maximum intensity t is the particle size l is the x-ray wavelength used q is the glancing angle of the X-ray beam with the crystal lattice plane in question.

It is relatively simple to directly compare the crystallinity of two compounds by comparing one or more reflections of the material's spectrum. For apatite, the reflection of the plane (300) is commonly used for this purpose. In many cases, the ratio of FWHM/M (M=peak intensity or peak height) is used for reporting crystallinity. Table 3 shows various parameters measured at day 22 and 29. Table 4 shows the femur's wet weight and length. There was no significant difference (Student T-test) between the control and theobromine group on any parameter measured (P>0.05). This is important since there was no indication in any parameters of the theobromine group of any adverse effects. We have concentrated on the plasma levels of Cu and Zn to see if any changes between the group occurred, since our studies on caffeine show decreased Zn and Cu concentrations in the plasma.

TABLE 3

Various parameters measured at days 22 and 29 postbirth (mean ± SEM)

|  | Control | Theobromine |
| --- | --- | --- |
| Dam's weight at day 22 (g) | 349 ± 13 (8) | 362 ± 7 (8) |
| Pup's weight at day 22 (g) | 73.9$^a$ ± 1.7 (8) | 72.8$^a$ ± 2.4 (8) |
| Male pup's weight at day 29 (g) | 124.1$^b$ ± 2.1 | 117.9$^b$ ± 2.6 (8) |
| Female pup's weight at day 29 (g) | 111.0$^b$ ± 2.4 (8) | 105.6$^b$ ± 2.5 (8) |
| Food intake/day/dam day 1–22 (g) | 53.6$^c$ ± 4.3 | 52.5$^c$ ± 3.6 |
| Food intake/day/pup day 22–29 (g) | 12.0$^d$ ± 0.9 | 12.1$^d$ ± 1.0 |
| Dam's plasma Zn at day 22 (mg/ml) | 1.36 ± 0.07 (6) | 1.40 ± 0.12 (7) |
| Pup's plasma Zn at day 22 (mg/ml) | 1.25$^e$ ± 0.08 (8) | 1.16$^e$ ± 0.03 (8) |
| Pup's plasma Zn at day 29 (mg/ml) | 1.12$^f$ ± 0.06 (7) | 0.99$^f$ ± 0.07 (8) |
| Dam's milk Zn at day 22 (mg/ml) | 11.07 ± 0.08 (6) | 11.75 ± 0.45 (7) |
| Dam's plasma Cu at day 22 (mg/ml) | 0.767 ± 0.045 (7) | 0.750 ± 0.061 (7) |
| Pup's plasma Cu at day 22 (mg/ml) | 0.638$^e$ ± 0.020 (8) | 0.652$^e$ ± 0.009 (7) |
| Pup's plasma Cu at day 29 (mg/ml) | 0.560$^f$ ± 0.021 (7) | 0.621$^f$ ± 0.047 (8) |
| Dam's milk Cu at day 22 (mg/ml) | 1.076 ± 0.045 (5) | 1.040 ± 0.115 (6) |

Parentheses indicate numbers measured.
[a] Averaged litter weight. Male and female pups were not distinguished during lactation.
[b] At day 22 pups were weaned. One male and one female pup were removed from each dam; however, we could not obtain one male pup from one dam at day 22.
[c] Dam's food intake was averaged until day 22. Around day 15 pups started nibbling dam's food.
[d] Pup's food intake after weaning at day 22.
[e] Each sample is pooled blood from the same litter. We could not measure one sample from the theobromine group for Cu determination due to shortage of blood plasma.
[f] There was no significant difference between male and female plasma values of Zn and Cu; therefore, data were combined. Pup's blood samples had to be pooled due to a shortage of blood plasma.

TABLE 4

Wet weight of femurs in rats at day 29 (mean ± SEM).

| Gender |  | Length | Wet weight |
| --- | --- | --- | --- |
| Male | Control | 2.09 ± .04 | .3949 ± .017 |
|  | Experimental | 2.06 ± .02 | .3991 ± .011 |
| Female | Control | 2.03 ± .02 | .3573 ± .008 |
|  | Experimental | 2.03 ± .02 | .3490 ± .011 |

The polished femurs of 29 day old rats also were analyzed on the microprobe following this procedure: areas of highest apatite density were determined by scanning the beam over a large area of bone. These highest Ca and P areas were then analyzed. This procedure was used to avoid analyzing organic materials.

The results are shown in Table 5. From these results it is evident that there is little difference in the actual composition of the bone material between the experimental and control groups.

TABLE 5

|  | Sample | Results (averages of 5 analyses): | |
| --- | --- | --- | --- |
|  |  | $P_2O_5$ weight percent | CaO weight percent |
| Experimental | 1012 (male) | 39.61 | 53.88 |
|  | 1011 (female) | 36.22 | 53.69 |
| Control | 1004 (male) | 36.50 | 53.49 |
|  | 1005 (female) | 36.31 | 53.78 |

The femurs from 29 day old female animals in the control and experimental groups were subjected to a mechanical property study. The femurs, which were kept in air tight glass bottles in the freezer, were defrosted. Mechanical properties were measured using an "Unstring"™ Universal Testing Instrument. Yield stress in megapascals (Mpa) was found to be 43653±2361 (mean±SEM), in the control group (N=10) and 48040±2660 in the experimental group (N=7). The experimental group showed an approximate 10% increase. Maximum (failure) stress was 21362±766 in the control (N=10) and 23577±1040 in the experimental group (N=7). The experimental group showed a 9% increase. Young's Modulus of Elasticity (Map) was 893837±79285 in the control (N=10) and 1081796±99123 in the experimental group (N=7). This showed about a 21% increase in the experimental group over the control. When yield stress, maximum stress and Young's modulus of elasticity are considered, one can conclude that female femurs in the experimental group were stronger and stiffer and show relatively less deformation under applied loading. Femur volume (ml) was 0.273±0.019 in the control (N=11) and 0.286±0.014 in the experimental group (N=7). This was about a 5% increase in the experimental group over the control.

For male, yield stress (Map) was 51388±3307 in the control (N=6) and 46212±2422 in the experimental group (N=8). This was about 10% decrease in the experimental group.

Maximum stress was 22830±1775 in the control (N=6) and 21235±847 in the experimental group (N=8). This was about 7% decrease in the experimental group. Young's modulus of elasticity (Map) was 1075678±8403 in the control (N=6) 1043988±43453 in the experimental group (N=8). This was about 3% decrease in the experimental group. These results indicate that male femurs in the experimental group are relatively weaker and less stiff and show greater deformation under applied loading.

EXAMPLE 4
Bone From Ovariectomized Females.

Figure 16:
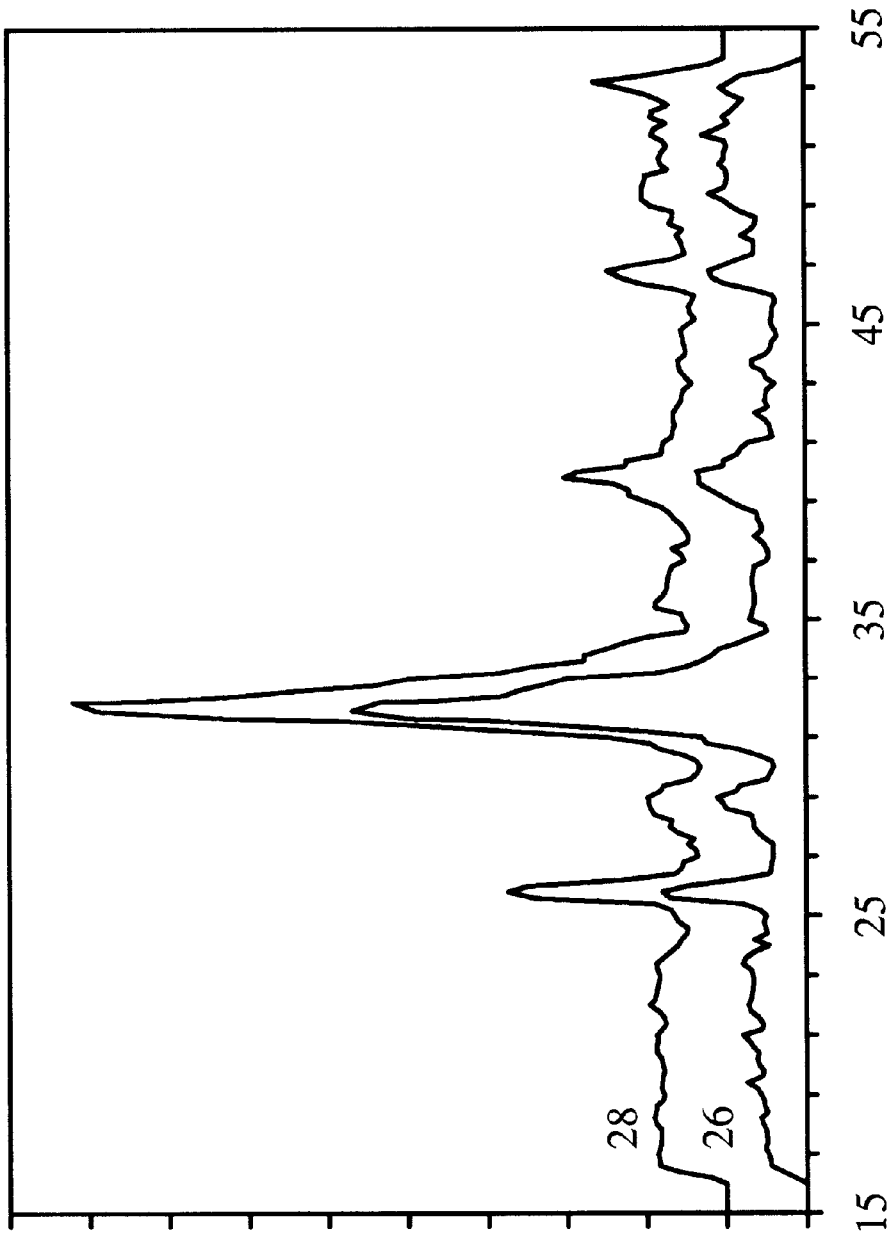
FIG. 16. X-ray diffraction scan of apatite obtained from the femur of an ovariectomized animal from the experimental group (upper tracing) and an ovariectomized animal from the control group (lower tracing).

Female rats were ovariectomized at day 30 and then those in the experimental group were fed a diet with the same amount of substance as previously used. The females in the control group were fed the diet without experimental substance. Both groups of animals were killed at day 69 or 70. Femurs were removed, powdered and examined with a "SCINTAG XDS 2000"™ X-ray diffractometer. This X-ray diffractometry of the female femurs showed larger crystallites in the experimental group (upper tracing) than in the control (FIG. 16).

SUMMARY OF FINDINGS

It is evident from the attached results that partially methylated xanthines enhance crystallinity in apatite grown in vitro. Our results indicate that theobromine enhances crystallinity in vivo, as well. The results of X-ray diffraction studies of bone and teeth indicate larger crystallite size, as noted by sharpening of the (300) reflections. Microprobe results do not indicate a more intense mineralization of either bone or tooth material. Scanning electron microscopy in vitro shows coarser apatite crystallites in the theobromine and 3-methyl xanthine group than in the control group. Evidently, no additional apatite material is deposited in either bones or teeth but the crystallite size is increased in the partially methylated xanthines, making such material less easily dissolved. Application of these compounds may have profound effects on the health of human bone and teeth.

All references cited herein, including journal articles or abstracts, published or corresponding U.S. or foreign patent applications, issued U.S. or foreign patents, or any other references, are entirely incorporated by reference herein, including all data, tables, figures, and text presented in the cited references. Additionally, the entire contents of the references cited within the references cited herein are also entirely incorporated by reference.

Reference to known method steps, conventional methods steps, known methods or conventional methods is not in any way an admission that any aspect, description or embodiment of the present invention is disclosed, taught or suggested in the relevant art.

The foregoing description of the specific embodiments will so fully reveal the general nature of the present invention that others can, by applying knowledge within the skill of the art (including the contents of the references cited herein), readily modify and/ or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

What is claimed is:

1. A method for increasing crystallite size of an apatite, thereby decreasing the angular range of x-rays diffracted therefrom, comprising the steps of:

providing a partially alkylated xanthine chosen from the group consisting of compounds of the formula:

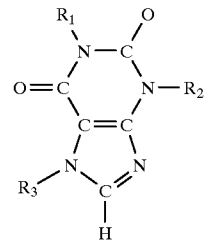

wherein a hydrogen comprises one of the R1, R2, and R3 substituents, and alkyl groups independently comprise two of the substituents; and contacting an apatite-forming-system with an amount of the partially alkylated xanthine sufficient to increase the crystallite size of the apatite formed therefrom; and maintaining an ambient temperature of about 15 to 45° C. for a period sufficient to crystallize apatite, and wherein the apatite forming system comprises a solution of CaCl2 and $Na_3PO_4$ at a pH of approximately 9–9.5.

2. The method of claim 1 wherein the xanthine is methylated.

3. A method for increasing crystallite size of an apatite, thereby decreasing the angular range of x-rays diffracted therefrom, comprising the steps of:

providing the partially alkylated xanthine of claim 1; and treating an animal capable of forming apatite with an amount of the partially alkylated xanthine sufficient to increase the crystallite size of the apatite formed therefrom.

4. The method of claim 3 wherein the mass of the apatite formed therefrom is increased.

5. The method of claim 3 wherein the xanthine is methylated.

6. A method for increasing strength of a biologically formed apatite composite, thereby increasing yield stress, maximum stress, or elasticity, the method comprising the steps of providing the partially alkylated xanthine of claim 1; and treating an animal capable of forming the apatite composite with an amount of the partially alkylated xanthine sufficient to increase the strength thereof, wherein the composite comprises apatite and collagen.

7. The method of claim 6 wherein the apatite composite comprises a bone.

8. The method of claim 6 wherein the apatite composite comprises a tooth.

* * * * *